(12) United States Patent
Kitajewski et al.

(10) Patent No.: US 11,026,996 B2
(45) Date of Patent: Jun. 8, 2021

(54) HUMAN NOTCH1 BASED FUSION PROTEINS AS DECOY INHIBITORS OF JAGGED-NOTCH SIGNALING AND DLL-NOTCH SIGNALING

(71) Applicant: The Trustees of Columbia University in the City of New York, New York, NY (US)

(72) Inventors: Jan Kitajewski, Ridgewood, NJ (US); Reyhaan Ali Chaudhri, Smyrna, GA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 88 days.

(21) Appl. No.: 16/304,595

(22) PCT Filed: May 25, 2017

(86) PCT No.: PCT/US2017/034521
§ 371 (c)(1),
(2) Date: Nov. 26, 2018

(87) PCT Pub. No.: WO2017/205651
PCT Pub. Date: Nov. 30, 2017

(65) Prior Publication Data
US 2019/0183975 A1    Jun. 20, 2019

Related U.S. Application Data

(60) Provisional application No. 62/341,331, filed on May 25, 2016.

(51) Int. Cl.
| | | |
|---|---|---|
| C07K 14/705 | (2006.01) |
| C07K 16/28 | (2006.01) |
| C07K 19/00 | (2006.01) |
| A61K 38/17 | (2006.01) |
| A61K 39/395 | (2006.01) |
| A61K 38/18 | (2006.01) |
| A61P 35/00 | (2006.01) |
| A61P 27/02 | (2006.01) |
| A61K 45/06 | (2006.01) |
| C12N 15/62 | (2006.01) |
| C12N 15/85 | (2006.01) |

(52) U.S. Cl.
CPC ........ *A61K 38/1866* (2013.01); *A61K 38/177* (2013.01); *A61K 39/3955* (2013.01); *A61K 45/06* (2013.01); *A61P 27/02* (2018.01); *A61P 35/00* (2018.01); *C07K 14/705* (2013.01); *C07K 16/283* (2013.01); *C07K 19/00* (2013.01); *C12N 15/62* (2013.01); *C12N 15/85* (2013.01); *C07K 2319/02* (2013.01); *C07K 2319/30* (2013.01)

(58) Field of Classification Search
CPC ............... A61K 38/177; A61K 38/179; A61K 38/1793; C07K 2319/30; C07K 14/705; C07K 2319/00; C07K 14/71; C07K 2319/32; C07K 14/715
See application file for complete search history.

(56) References Cited

U.S. PATENT DOCUMENTS

| | | | | |
|---|---|---|---|---|
| 7,488,806 | B2* | 2/2009 | Papadopoulos | A61P 37/06 |
| | | | | 530/388.15 |
| 7,803,377 | B2* | 9/2010 | Yan | A61P 1/04 |
| | | | | 424/145.1 |
| 8,435,513 | B2* | 5/2013 | Gurney | C07K 16/3046 |
| | | | | 424/130.1 |
| 9,090,690 | B2* | 7/2015 | Li | A61K 39/395 |
| 9,518,121 | B2* | 12/2016 | Chinn | A61P 1/00 |
| 9,982,058 | B2* | 5/2018 | French | A61P 35/00 |
| 2005/0261477 | A1 | 11/2005 | Champion et al. | |
| 2008/0014196 | A1* | 1/2008 | Yan | A61P 37/06 |
| | | | | 424/133.1 |
| 2008/0187532 | A1* | 8/2008 | Gurney | A61K 45/06 |
| | | | | 424/133.1 |
| 2014/0271643 | A1 | 9/2014 | Kitajewski et al. | |
| 2015/0329615 | A1 | 11/2015 | Kitajewski et al. | |

(Continued)

OTHER PUBLICATIONS

Funahashi et al. A Notch1 ectodomain construct inhibits endothelial Notch signaling, tumor growth, and angiogenesis. Cancer Res 68(12): 4727-4735, 2008.*
Kangsamaksin et al. NOTCH decoys that selectively block DLL/NOTCH or JAG/NOTCH disrupt angiogenesis by unique mechanisms to inhibit tumor growth. Cancer Discovery 5(2): 182-197, 2015 (online Nov. 11, 2014).*

(Continued)

*Primary Examiner* — Bridget E Bunner
(74) *Attorney, Agent, or Firm* — John P. White

(57) ABSTRACT

This invention provides a fusion protein, the sequence of which, commencing at the N-terminus of the fusion protein, is identical to the sequence of amino acids in:
(a) an extracellular domain of a human Notch1 receptor protein, followed by
(b) an Fc portion of an antibody,
wherein the extracellular domain of the human Notch1 receptor protein
(i) commences with the amino acid present at the N-terminus of EGF-like repeat 10 and
(ii) extends to and includes the C-terminal amino acid of EGF-like repeat 18 or 20.

Also provided is a composition comprising the any of the fusion proteins of this invention and a pharmaceutically acceptable carrier, a method of treating a subject suffering from age-related macular degeneration (AMD), diabetic retinopathy, or cancer which comprises administering to the subject any of the compositions of this invention in an amount effective to treat the subject's cancer.

11 Claims, 14 Drawing Sheets

Specification includes a Sequence Listing.

(56) References Cited

U.S. PATENT DOCUMENTS

2016/0030513 A1  2/2016  Pajvani et al.
2016/0115217 A1  4/2016  Kitajewski et al.

OTHER PUBLICATIONS

Li et al. The Notch ligand Jagged1 as a target for anti-tumor therapy. Front Oncol 4: article 254, 2014 (13 total pages).*
Noguera-Troise et al. Blockade of Dll4 inhibits tumour growth by promoting non-productuve angiogenesis. Nature 444:1032-1037, 2006.*
Nowak et al. Age-related macular degeneration (AMD): pathogenesis and therapy. Pharmacol Rep 58: 353-363, 2006.*
Ridgway et al. Inhibition of Dll4 signalling inhibits tumour growth by deregulating angiogenesis. Nature 444: 1083-1087, 2006.*
Simo et al. Angiogenic and antiangiogenic factors in proliferative diabetic retinopathy. Curr Diab Rev 2: 71-98, 2006.*
Wu et al. Therapeutic antibody targeting of individual Notch receptors. Nature 464: 1052-1057, 2010 (8 total pages).*
Yu et al. Pathogenesis and intervention strategies in diabetic retinopathy. Clin Exp Ophthalmol 29: 164-166, 2001.*
International Search Report in connection with PCT International Application No. PCT/US2017/034,521.
Written Opinion of the International Searching Authority in connection with the PCT International Application No. PCT/US2017/034,521.

* cited by examiner

Figure 1A:

Human NOTCH1 Protein Sequence (SEQ ID NO:1)

```
        SP                         EGF-Like Repeat 1

1 MPPLLAPLLC LALLPALAAR GPRCSQPGET CLNGGKCEAA NGTEACVCGG AFVGPRCQDP 2                                          3

61 NPCLSTPCKN AGTCHVVDRR GVADYACSCA LGFSGPLCLT PLDNACLTNP CRNGGTCDLL

4

121 TLTEYKCRCP PGWSGKSCQQ ADPCASNPCA NGGQCLPFEA SYICHCPPSF HGPTCRQDVN 5                                          6

181 ECGQKPGLCR HGGTCHNEVG SYRCVCRATH TGPNCERPYV PCSPSPCQNG GTCRPTGDVT 7                                 8

241 HECACLPGFT GQNCEENIDD CPGNNCKNGG ACVDGVNTYN CRCPPEWTGQ YCTEDVDECQ

9

301 LMPNACQNGG TCHNTHGGYN CVCVNGWTGE DCSENIDDCA SAACFHGATC HDRVASFYCE 10                                          11

361 CPHGRTGLLC HLNDACISNP CNEGSNCDTN PVNGKAICTC PSGYTGPACS QDVDECSLGA

12

421 NPCEHAGKCI NTLGSFECQC LQGYTGPRCE IDVNECVSNP CQNDATCLDQ IGEFQCICMP 13                                          14

481 GYEGVHCEVN TDECASSPCL HNGRCLDKIN EFQCECPTGF TGHLCQYDVD ECASTPCKNG

15

541 AKCLDGPNTY TCVCTEGYTG THCEVDIDEC DPDPCHYGSC KDGVATFTCL CRPGYTGHHC 16                                          17

601 ETNINECSSQ PCRHGGTCQD RDNAYLCFCL KGTTGPNCEI NLDDCASSPC DSGTCLDKID 18                                19

661 GYECACEPGY TGSMCNINID ECAGNPCHNG GTCEDGINGF TCRCPEGYHD PTCLSEVNEC

20

721 NSNPCVHGAC RDSLNGYKCD CDPGWSGTNC DINNNECESN PCVNGGTCKD MTSGYVCTCR 21                                22
```

Exhibit A

Figure 1B

```
 781 EGFSGPNCQT NINECASNPC LNQGTCIDDV AGYKCNCLLP YTGATCEVVL APCAPSPCRN
                                        23
 841 GGECRQSEDY ESFSCVCPTG WQGQTCEVDI NECVLSPCRH GASCQNTHGG YRCHCQAGYS
                24                                         25
 901 GRNCETDIDD CRPNPCHNGG SCTDGINTAF CDCLPGFRGT FCEEDINECA SDPCRNGANC
                                        26
 961 TDCVDSYTCT CPAGFSGIHC ENNTPDCTES SCFNGGTCVD GINSFTCLCP PGFTGSYCQH
                27                                         28
1021 DVNECDSQPC LHGGTCQDGC GSYRCTCPQG YTGPNCQNLV HWCDSSPCKN GGKCWQTHTQ
                                        29
1081 YRCECPSGWT GLYCDVPSVS CEVAAQRQGV DVARLCQHGG LCVDAGNTHH CRCQAGYTGS
                30                                         31
1141 YCEDLVDECS PSPCQNGATC TDYLGGYSCK CVAGYHGVNC SEEIDECLSH PCQNGGTCLD
                                        32
1201 LPNTYKCSCP RGTQGVHCEI NVDDCNPPVD PVSRSPKCFN NGTCVDQVGG YSCTCPPGFV
                33                                         34
1261 GERCEGDVNE CLSNPCDARG TQNCVQRVND FHCECRAGHT GRRCESVING CKGKPCKNGG
                                        35
1321 TCAVASNTAR GFICKCPAGF EGATCENDAR TCGSLRCLNG GTCISGPRSP TCLCLGPFTG
                36                                         |
1381 PECQFPASSP CLGGNPCYNQ GTCEPTSESP FYRCLCPAKF NGLLCHILDY SFGGGAGRDI
               LNR 1                                       2
1441 PPPLIEEACE LPECQEDAGN KVCSLQCNNH ACGWDGGDCS LNFNDPWKNC TQSLQCWKYF
                                         3
1501 SDGHCDSQCN SAGCLFDGFD CQRAEGQCNP LYDQYCKDHF SDGHCDQGCN SAECEWDGLD
       |
1561 CAEHVPERLA AGTLVVVVLM PPEQLRNSSF HFLRELSRVL HTNVVFKRDA HGQQMIFPYY
                                         S1
```

Figure 1C

```
1621 GREEELRKHP IKRAAEGWAA PDALLGQVKA SLLPGGSEGG RRRRELDPMD VRGSIVYLEI
                                                      S2              TM
1681 DNRQCVQASS QCFQSATDVA AFLGALASLG SLNIPYKIEA VQSETVEPPP PAQLHFMYVA
                    S3
1741 AAAFVLLFFV GCGVLLSRKR RRQHGQLWFP EGFKVSEASK KKRREPLGED SVGLKPLKNA

1801 SDGALMDDNQ NEWGDEDLET KKFRFEEPVV LPDLDDQTDH RQWTQQHLDA ADLRMSAMAP

1861 TPPQGEVDAD CMDVNVRGPD GFTPLMIASC SGGGLETGNS EEEEDAPAVI SDFIYQGASL
        ANK Repeat 1
1921 HNQTDRTGET ALHLAARYSR SDAAKRLLEA SADANIQDNM GRTPLHAAVS ADAQGVFQIL

1981 IRNRATDLDA RMHDGTTPLI LAARLAVEGM LEDLINSHAD VNAVDDLGKS ALHWAAAVNN

2041 VDAAVVLLKN GANKDMQNNR EETPLFLAAR EGSYETAKVL LDHFANRDIT DHMDRLPRDI
                  |
2101 AQERMHHDIV RLLDEYNLVR SPQLHGAPLG GTPTLSPPLC SPNGYLGSLK PGVQGKKVRK

2161 PSSKGLACGS KEAKDLKARR KKSQDGKGCL LDSSGMLSPV DSLESPHGYL SDVASPPLLP

2221 SPFQQSPSVP LNHLPGMPDT HLGIGHLNVA AKPEMAALGG GGRLAFETGP PRLSHLPVAS

2281 GTSTVLGSSS GGALNFTVGG STSLNGQCEW LSRLQSGMVP NQYNPLRGSV APGPLSTQAP

2341 SLQHGMVGPL HSSLAASALS QMMSYQGLPS TRLATQPHLV QTQQVQPQNL QMQQQNLQPA

2401 NIQQQQSLQP PPPPPQPHLG VSSAASGHLG RSFLSGEPSQ ADVQPLGPSS LAVHTILPQE
                                                                 PEST
```

Figure 1D

2461 SPALPTSLPS SLVPPVTAAQ FLTPPSQHSY SSPVDNTPSH QLQVPEHPFL TPSPESPDQW

2521 SSSSPHSNVS DWSEGVSSPP TSMQSQIARI PEAFK

Figure 2A:

Notch1 Decoy 10-24 (2502)

Human Notch1 signal peptide: 1-69

EGF-like repeats 10-24: 70-1788

Human Fc: 1789-2502

DNA Sequence (SEQ ID NO:2)

```
   1 ATGCCGCCGC TCCTGGCGCC CCTGCTCTGC CTGGCGCTGC TGCCCGCGCT CGCCGCACGA
  61 GGCCCGCGAT GCATCAGCAA CCCCTGTAAC GAGGGCTCCA ACTGCGACAC CAACCCTGTC
 121 AATGGCAAGG CCATCTGCAC CTGCCCCTCG GGGTACACGG GCCCGGCCTG CAGCCAGGAC
 181 GTGGATGAGT GCTCGCTGGG TGCCAACCCC TGCGAGCATG CGGGCAAGTG CATCAACACG
 241 CTGGGCTCCT TCGAGTGCCA GTGTCTGCAG GGCTACACGG GCCCCCGATG CGAGATCGAC
 301 GTCAACGAGT GCGTCTCGAA CCCGTGCCAG AACGACGCCA CCTGCCTGGA CCAGATTGGG
 361 GAGTTCCAGT GCATCTGCAT GCCCGGCTAC GAGGGTGTGC ACTGCGAGGT CAACACAGAC
 421 GAGTGTGCCA GCAGCCCCTG CCTGCACAAT GGCCGCTGCC TGGACAAGAT CAATGAGTTC
 481 CAGTGCGAGT GCCCCACGGG CTTCACTGGG CATCTGTGCC AGTACGATGT GGACGAGTGT
 541 GCCAGCACCC CCTGCAAGAA TGGTGCCAAG TGCCTGGACG GACCCAACAC TTACACCTGT
 601 GTGTGCACGG AAGGGTACAC GGGGACGCAC TGCGAGGTGG ACATCGATGA GTGCGACCCC
 661 GACCCCTGCC ACTACGGCTC CTGCAAGGAC GGCGTCGCCA CCTTCACCTG CCTCTGCCGC
 721 CCAGGCTACA CGGGCCACCA CTGCGAGACC AACATCAACG AGTGCTCCAG CCAGCCCTGC
 781 CGCCACGGGG GCACCTGCCA GGACCGCGAC AACGCCTACC TCTGCTTCTG CCTGAAGGGG
 841 ACCACAGGAC CCAACTGCGA GATCAACCTG GATGACTGTG CCAGCAGCCC CTGCGACTCG
 901 GGCACCTGTC TGGACAAGAT CGATGGCTAC GAGTGTGCCT GTGAGCCGGG CTACACAGGG
 961 AGCATGTGTA ACATCAACAT CGATGAGTGT GCGGGCAACC CCTGCCACAA CGGGGGCACC
1021 TGCGAGGACG GCATCAATGG CTTCACCTGC CGCTGCCCCG AGGGCTACCA CGACCCCACC
1081 TGCCTGTCTG AGGTCAATGA GTGCAACAGC AACCCCTGCG TCCACGGGGC CTGCCGGGAC
1141 AGCCTCAACG GGTACAAGTG CGACTGTGAC CCTGGGTGGA GTGGGACCAA CTGTGACATC
1201 AACAACAATG AGTGTGAATC CAACCCTTGT GTCAACGGCG GCACCTGCAA AGACATGACC
1261 AGTGGCTACG TGTGCACCTG CCGGGAGGGC TTCAGCGGTC CCAACTGCCA GACCAACATC
1321 AACGAGTGTG CGTCCAACCC ATGTCTGAAC CAGGGCACGT GTATTGACGA CGTTGCCGGG
1381 TACAAGTGCA ACTGCCTGCT GCCCTACACA GGTGCCACGT GTGAGGTGGT GCTGGCCCCG
```

Figure 2B

```
1441 TGTGCCCCCA GCCCCTGCAG AAACGGCGGG GAGTGCAGGC AATCCGAGGA CTATGAGAGC
1501 TTCTCCTGTG TCTGCCCCAC GGGCTGGCAA GGGCAGACCT GTGAGGTCGA CATCAACGAG
1561 TGCGTTCTGA GCCCGTGCCG GCACGGCGCA TCCTGCCAGA ACACCCACGG CGGCTACCGC
1621 TGCCACTGCC AGGCCGGCTA CAGTGGGCGC AACTGCGAGA CCGACATCGA CGACTGCCGG
1681 CCCAACCCGT GTCACAACGG GGGCTCCTGC ACAGACGGCA TCAACACGGC CTTCTGCGAC
1741 TGCCTGCCCG GCTTCCGGGG CACTTTCTGT GAGGAGGACA TCAACGAGGA TCTGGGCCCG
1801 GGCGAGCCCA ATCTTGTGA CAAAACTCAC ACATGCCCAC CGTGCCCAGC ACCTGAACTC
1861 CTGGGGGGAC CGTCAGTCTT CCTCTTCCCC CCAAAACCCA AGGACACCCT CATGATCTCC
1921 CGGACCCCTG AGGTCACATG CGTGGTGGTG GACGTGAGCC ACGAAGACCC TGAGGTCAAG
1981 TTCAACTGGT ACGTGGACGG CGTGGAGGTG CATAATGCCA AGACAAAGCC GCGGGAGGAG
2041 CAGTACAACA GCACGTACCG TGTGGTCAGC GTCCTCACCG TCCTGCACCA GGACTGGCTG
2101 AATGGCAAGG AGTACAAGTG CAAGGTCTCC AACAAAGCCC TCCCAGCCCC CATCGAGAAA
2161 ACCATCTCCA AAGCCAAAGG GCAGCCCCGA GAACCACAGG TGTACACCCT GCCCCCATCC
2221 CGGGAGGAGA TGACCAAGAA CCAGGTCAGC CTGACCTGCC TGGTCAAAGG CTTCTATCCC
2281 AGCGACATCG CCGTGGAGTG GGAGAGCAAT GGGCAGCCGG AGAACAACTA CAAGACCACG
2341 CCTCCCGTGC TGGACTCCGA CGGCTCCTTC TTCCTCTACA GCAAGCTCAC CGTGGACAAG
2401 AGCAGGTGGC AGCAGGGGAA CGTCTTCTCA TGCTCCGTGA TGCATGAGGC TCTGCACAAC
2461 CACTACACGC AGAAGAGCCT CTCCCTGTCT CCGGGTAAAT GA
```

Protein Sequence (SEQ ID NO:3)

```
  1 MPPLLAPLLC LALLPALAAR GPRCISNPCN EGSNCDTNPV NGKAICTCPS GYTGPACSQD
 61 VDECSLGANP CEHAGKCINT LGSFECQCLQ GYTGPRCEID VNECVSNPCQ NDATCLDQIG
121 EFQCICMPGY EGVHCEVNTD ECASSPCLHN GRCLDKINEF QCECPTGFTG HLCQYDVDEC
181 ASTPCKNGAK CLDGPNTYTC VCTEGYTGTH CEVDIDECDP DPCHYGSCKD GVATFTCLCR
241 PGYTGHHCET NINECSSQPC RHGGTCQDRD NAYLCFCLKG TTGPNCEINL DDCASSPCDS
301 GTCLDKIDGY ECACEPGYTG SMCNINIDEC AGNPCHNGGT CEDGINGFTC RCPEGYHDPT
361 CLSEVNECNS NPCVHGACRD SLNGYKCDCD PGWSGTNCDI NNNECESNPC VNGGTCKDMT
421 SGYVCTCREG FSGPNCQTNI NECASNPCLN QGTCIDDVAG YKCNCLLPYT GATCEVVLAP
481 CAPSPCRNGG ECRQSEDYES FSCVCPTGWQ GQTCEVDINE CVLSPCRHGA SCQNTHGGYR
```

Figure 2C

```
541 CHCQAGYSGR NCETDIDDCR PNPCHNGGSC TDGINTAFCD CLPGFRGTFC EEDINEDLGP
601 GEPKSCDKTH TCPPCPAPEL LGGPSVFLFP PKPKDTLMIS RTPEVTCVVV DVSHEDPEVK
661 FNWYVDGVEV HNAKTKPREE QYNSTYRVVS VLTVLHQDWL NGKEYKCKVS NKALPAPIEK
721 TISKAKGQPR EPQVYTLPPS REEMTKNQVS LTCLVKGFYP SDIAVEWESN GQPENNYKTT
781 PPVLDSDGSF FLYSKLTVDK SRWQQGNVFS CSVMHEALHN HYTQKSLSLS PGK*
```

DLL4-specific: Notch1 1-13
JAG1-specific: Notch1 10-24
JAG1-specific: Notch1 10-20

DAPT: Gamma secretase inhibitor
Fc: Decoy Control
DLL4-specific: Notch1 1-13
JAG1-specific: Notch1 10-24
JAG1-specific: Notch1 10-20

HUMAN NOTCH1 BASED FUSION PROTEINS AS DECOY INHIBITORS OF JAGGED-NOTCH SIGNALING AND DLL-NOTCH SIGNALING

GOVERNMENT SUPPORT

This invention was made with government support under grant number 1R01 HL112626 awarded by the National Institutes of Health. The government has certain rights in the invention.

CROSS-REFERENCE TO RELATED APPLICATIONS

This application is a § 371 national stage of PCT International Application No. PCT/US2017/034,521, filed May 25, 2018, claiming the benefit of U.S. Provisional Application No. 62/341,331 filed May 25, 2016, the contents of each of which are hereby incorporated herein by reference into the application.

Throughout this application, various publications are referenced by author and publication date within parentheses. Full citations for these publications may be found at the end of the specification or at the end of each experimental section. The disclosures of these publications are hereby incorporated by reference into this application to describe more fully the art to which this invention pertains.

REFERENCE TO A SEQUENCE LISTING

This application incorporates-by-reference nucleotide and/or amino acid sequences which are present in the file named "181126_88010-A-PCT-US_Sequence_Listing_CAS.txt", which is 32.6 kilobytes in size, and was created Nov. 21, 2018 in the IBM-PC machine format, having an operating system capacity with MS-Windows, which is contained in the text file being filed Nov. 26, 2018 as part of this application.

BACKGROUND OF THE INVENTION

Notch proteins play key roles in developmental decisions involving the vasculature, the hematopoietic system, and the nervous system. As such, an understanding of their function is key to understanding how cell-fate decisions and commitment are controlled during development and in adult tissues. To date, several reports on Notch or Notch ligand gene disruptions have described vascular phenotypes providing emphasis that this pathway is a fundamental part of the machinery that guides vascular development. Aberrant Notch activity has been linked to human pathologies; including both cancer and vascular disorders (CADASIL). The analysis of Notch in tumor angiogenesis has only recently begun; however, our discovery of potential downstream targets of Notch suggests a role in pathological processes associated with angiogenesis. For instance, VEGFR-3 has been linked to both tumor angiogenesis and tumor lymphangiogenesis. The expression or function of several other potential Notch targets has also been linked to tumor angiogenesis; including ephrinB2, Id3, Angiopoietin 1, and PDGF-B. Insights on the role of these targets in Notch gene function will clearly facilitate future analysis of Notch in human pathologies.

SUMMARY OF THE INVENTION

This invention provides a fusion protein, the sequence of which, commencing at the N-terminus of the fusion protein, is identical to the sequence of amino acids in:
(a) an extracellular domain of a human Notch1 receptor protein, followed by
(b) an Fc portion of an antibody,
wherein the extracellular domain of the human Notch1 receptor protein
 (i) commences with the amino acid present at the N-terminus of EGF-like repeat 10 and
 (ii) extends to and includes the C-terminal amino acid of EGF-like repeat 18.

Also provided is a fusion protein, the sequence of which, commencing at the N-terminus of the fusion protein, is identical to the sequence of amino acids in:
(a) an extracellular domain of a human Notch1 receptor protein, followed by
(b) an Fc portion of an antibody,
wherein the extracellular domain of the human Notch1 receptor protein
 (i) commences with the amino acid present at the N-terminus of EGF-like repeat 10 and
 (ii) extends to and includes the C-terminal amino acid of EGF-like repeat 20.

Also provided is a fusion protein, the sequence of which, commencing at the N-terminus of the fusion protein, is identical to the sequence of amino acids in:
(a) an extracellular domain of a human Notch1 receptor protein, followed by
(b) a linker sequence, followed by
(c) an Fc portion of an antibody,
wherein the extracellular domain of the human Notch1 receptor protein
 (i) commences with the amino acid present at the N-terminus of EGF-like repeat 10 and
 (ii) extends to and includes the C-terminal amino acid of EGF-like repeat 18.

Also provided is a fusion protein, the sequence of which, commencing at the N-terminus of the fusion protein, is identical to the sequence of amino acids in:
(a) an extracellular domain of a human Notch1 receptor protein, followed by
(b) a linker sequence, followed by
(c) an Fc portion of an antibody,
wherein the extracellular domain of the human Notch1 receptor protein
 (i) commences with the amino acid present at the N-terminus of EGF-like repeat 10 and
 (ii) extends to and includes the C-terminal amino acid of EGF-like repeat 20.

Also provided is a fusion protein the sequence of which, commencing at the N-terminus of the fusion protein, is identical to the sequence of amino acids in:
(a) a signal peptide, followed by
(b) an extracellular domain of a human Notch1 receptor protein, followed by
(c) an Fc portion of an antibody,
wherein the extracellular domain of the human Notch1 receptor protein
 (i) commences with the amino acid present at the N-terminus of EGF-like repeat 10 and
 (ii) extends to and includes the C-terminal amino acid of EGF-like repeat 18.

Also provided is a fusion protein the sequence of which, commencing at the N-terminus of the fusion protein, is identical to the sequence of amino acids in:
  (a) a signal peptide, followed by
  (b) an extracellular domain of a human Notch1 receptor protein, followed by
  (c) an Fc portion of an antibody,
wherein the extracellular domain of the human Notch1 receptor protein
  (i) commences with the amino acid present at the N-terminus of EGF-like repeat 10 and
  (ii) extends to and includes the C-terminal amino acid of EGF-like repeat 20.

Also provided is a composition comprising the any of the fusion proteins of this invention and a pharmaceutically acceptable carrier.

Also provided is a method of treating a subject suffering from age-related macular degeneration (AMD) which comprises administering to the subject any of the compositions of the invention in an amount effective to treat the subject's AMD.

Also provided is a method of treating a subject suffering from diabetic retinopathy which comprises administering to the subject any of the compositions of the invention in an amount effective to treat the subject's diabetic retinopathy.

Also provided is a method of treating a subject suffering from cancer which comprises administering to the subject any of the compositions of this invention in an amount effective to treat the subject's cancer.

BRIEF DESCRIPTION OF THE FIGURES

FIGS. 1A-1D: The amino acids sequence of the human NOTCH1 protein (SEQ ID NO:1).

FIGS. 2A-2C: The nucleic acid sequence of human Notch1 decoy 10-24 is set forth in SEQ ID NO:2. Human Notch 1 signal peptides corresponds to nucleotides 1-69 of SEQ ID NO:2, EGF-like repeats 10-24 correspond to nucleotides 70-1788 of SEQ ID NO:2 and Human Fc corresponds to nucleotides 1789-2502 of SEQ ID NO:2. The amino acid sequence of human Notch1 decoy 10-24 is set forth in SEQ ID NO:3.

DETAILED DESCRIPTION OF THE INVENTION

Terms

Figure 3:
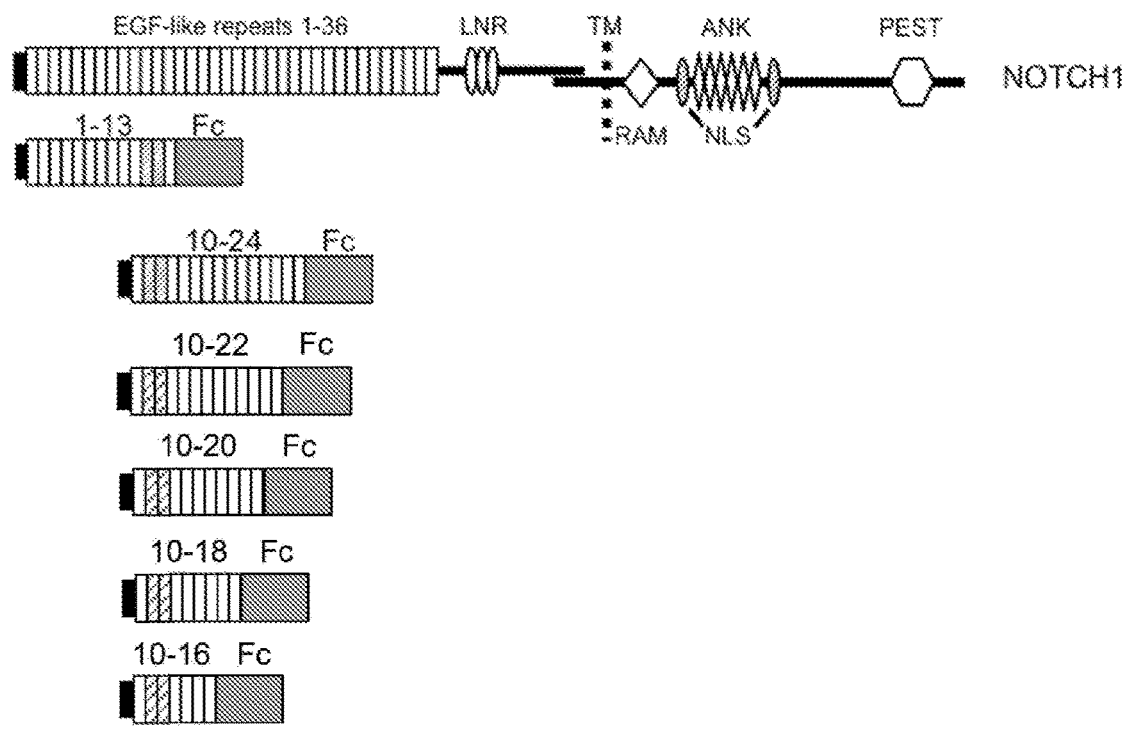
FIG. 3: Schematic of design of Notch1 Decoys.

As used in this application, except as otherwise expressly provided herein, each of the following terms shall have the meaning set forth below.

"Administering" may be effected or performed using any of the methods known to one skilled in the art. The methods comprise, for example, intralesional, intramuscular, subcutaneous, intravenous, intraperitoneal, liposome-mediated, transmucosal, intestinal, topical, nasal, oral, anal, ocular or otic means of delivery.

"Affixed" shall mean attached by any means. In one embodiment, affixed means attached by a covalent bond. In another embodiment, affixed means attached non-covalently.

"Amino acid," "amino acid residue" and "residue" are used interchangeably herein to refer to an amino acid that is incorporated into a protein, polypeptide or peptide. The amino acid can be, for example, a naturally occurring amino acid or an analog of a natural amino acid that can function in a manner similar to that of the naturally occurring amino acid.

"C-terminal" and "N-terminal" amino acid, as used herein, refers to an amino acids at or in close proximity to the carboxy or amino terminal ends, respectively, of a given protein, protein domain or amino acid sequence motif such that no amino acid residue essential to the structure, function, or characterization of the protein, protein domain or amino acid sequence motif lie beyond said C-terminal amino acid or N-terminal amino acid.

"Antibody" shall include, without limitation, (a) an immunoglobulin molecule comprising two heavy chains and two light chains and which recognizes an antigen; (b) a polyclonal or monoclonal immunoglobulin molecule; and (c) a monovalent or divalent fragment thereof. Immunoglobulin molecules may derive from any of the commonly known classes, including but not limited to IgA, secretory IgA, IgG, IgE and IgM. IgG subclasses are well known to those in the art and include, but are not limited to, human IgG1, IgG2, IgG3 and IgG4. Antibodies can be both naturally occurring and non-naturally occurring. Furthermore, antibodies include chimeric antibodies, wholly synthetic antibodies, single chain antibodies, and fragments thereof. Antibodies may be human or nonhuman. Nonhuman antibodies may be humanized by recombinant methods to reduce their immunogenicity in humans. Antibody fragments include, without limitation, Fab and Fc fragments. The "Fc portion of an antibody", in one embodiment, is a crystallizable fragment obtained by papain digestion of immunoglobulin that consists of the C-terminal half of two heavy chains linked by disulfide bonds and known as the "effector region" of the immunoglobulin. In another embodiment, "Fc portion of an antibody" means all, or substantially all, of one C-terminal half of a heavy chain.

"Humanized", with respect to an antibody, means an antibody wherein some, most or all of the amino acids outside the CDR region are replaced with corresponding amino acids derived from a human immunoglobulin molecule. Small additions, deletions, insertions, substitutions or modifications of amino acids are permissible as long as they do not abrogate the ability of the antibody to bind a given antigen. Suitable human immunoglobulin molecules include, without limitation, IgG1, IgG2, IgG3, IgG4, IgA and IgM molecules. Various publications describe how to make humanized antibodies, e.g., U.S. Pat. Nos. 4,816,567, 5,225,539, 5,585,089 and 5,693,761, and PCT International Publication No. WO 90/07861.

As used herein, the term "composition", as in pharmaceutical composition, is intended to encompass a product comprising the active ingredient(s) and the inert ingredient(s) that make up the carrier, as well as any product which results, directly or indirectly from combination, complexation, or aggregation of any two or more of the ingredients, or from dissociation of one or more of the ingredients, or from other types of reactions or interactions of one or more of the ingredients.

As used herein, "effective amount" refers to an amount which is capable of treating a subject having a tumor, a disease or a disorder. Accordingly, the effective amount will vary with the subject being treated, as well as the condition to be treated. A person of ordinary skill in the art can perform routine titration experiments to determine such sufficient amount. The effective amount of a compound will vary depending on the subject and upon the particular route of administration used. Based upon the compound, the amount can be delivered continuously, such as by continuous pump, or at periodic intervals (for example, on one or more separate occasions). Desired time intervals of multiple amounts of a particular compound can be determined without undue experimentation by one skilled in the art. In one embodiment, the effective amount is between about 1 µg/kg-10 mg/kg. In another embodiment, the effective amount is between about 10 µg/kg-1 mg/kg. In a further embodiment, the effective amount is 100 µg/kg.

"Extracellular domain" as used in connection with Notch receptor protein means all or a portion of Notch which (i) exists extracellularly (i.e. exists neither as a transmembrane portion or an intracellular portion) and (ii) binds to extracellular ligands to which intact Notch receptor protein binds. The extracellular domain of Notch may optionally include a signal peptide ("sp"). "Extracellular domain", "ECD" and "Ectodomain" are synonymous.

"Inhibiting" the onset of a disorder or undesirable biological process shall mean either lessening the likelihood of the disorder's or process' onset, or preventing the onset of the disorder or process entirely. In the preferred embodiment, inhibiting the onset of a disorder or process means preventing its onset entirely.

"Notch", "Notch protein", and "Notch receptor protein" are synonymous. In addition, the terms "Notch-based fusion protein" and "Notch decoy" are synonymous. The following Notch amino acid sequences are known and hereby incorporated by reference: Notch1 (Genbank accession no. S18188 (rat)); Notch2 (Genbank accession no. NP_077334 (rat)); Notch3 (Genbank accession no. Q61982 (mouse)); and Notch4 (Genbank accession no. T09059 (mouse)). The following Notch nucleic acid sequences are known and hereby incorporated by reference: Notch1 (Genbank accession no. XM_342392 (rat) and NM_017617 (human)); Notch2 (Genbank accession no. NM_024358 (rat), M99437 (human and AF308601 (human)); Notch3 (Genbank accession no. NM_008716 (mouse) and XM_009303 (human)); and Notch4 (Genbank accession no. NM_010929 (mouse) and NM_004557 (human)).

The terms "nucleic acid", "polynucleotide" and "nucleic acid sequence" are used interchangeably herein, and each refers to a polymer of deoxyribonucleotides and/or ribonucleotides. The deoxyribonucleotides and ribonucleotides can be naturally occurring or synthetic analogues thereof. "Nucleic acid" shall mean any nucleic acid, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA). Nucleic acids include, without limitation, anti-sense molecules and catalytic nucleic acid molecules such as ribozymes and DNAzymes. Nucleic acids also include nucleic acids coding for peptide analogs, fragments or derivatives which differ from the naturally-occurring forms in terms of the identity of one or more amino acid residues (deletion analogs containing less than all of the specified residues; substitution analogs wherein one or more residues are replaced by one or more residues; and addition analogs, wherein one or more resides are added to a terminal or medial portion of the peptide) which share some or all of the properties of the naturally-occurring forms.

The terms "polypeptide," "peptide" and "protein" are used interchangeably herein, and each means a polymer of amino acid residues. The amino acid residues can be naturally occurring or chemical analogues thereof. Polypeptides, peptides and proteins can also include modifications such as glycosylation, lipid attachment, sulfation, hydroxylation, and ADP-ribosylation.

As used herein, "pharmaceutically acceptable carrier" means that the carrier is compatible with the other ingredients of the formulation and is not deleterious to the recipient thereof, and encompasses any of the standard pharmaceutically accepted carriers. Such carriers include, for example, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

"Subject" shall mean any organism including, without limitation, a mammal such as a mouse, a rat, a dog, a guinea pig, a ferret, a rabbit and a primate. In one embodiment, the subject is a human.

"Treating" means either slowing, stopping or reversing the progression of a disease or disorder. As used herein, "treating" also means the amelioration of symptoms associated with the disease or disorder. Diseases include, but are not limited to, Tumor Angiogenesis, Atherosclerosis, Wound Healing, Retinopathy of Prematurity, Pre-eclampsia, Diabetic retinopathy, Ischemia, Stroke, Cardiovascular Disease, Psoriasis, lymphedema, tumorigenesis and tumor lymphangiogenesis, age-related macular degeneration (AMD), wet AMD, pancreatic cancer and breast cancer.

Angiogenesis is encountered during wound healing processes, the female menstrual cycle and endometrial remodeling, as well as during embryonic development and organ growth. In the pathological setting, angiogenesis plays an important role in different diseases like rheumatoid arthritis, psoriasis, macular degeneration, diabetic retinopathy, and tumor growth.

There has been considerable evidence in vivo, including clinical observations, that abnormal angiogenesis is implicated in a number of disease conditions, which include rheumatoid arthritis, inflammation, cancer, psoriasis, degenerative eye conditions and others.

Other diseases for use of Notch fusion proteins are metabolic disorders such as, but not limited to, Diabetes, Obesity, Prediabetic state, Atherosclerosis, Ischemia, Stroke, Cardiovascular Disease, Regulating expression of Insulin, and Regulating the function of Insulin.

The use of Notch fusion proteins is also indicated for Metabolic Syndrome refers to a combination of medical disorders that increases the risk to a person for cardiovascular disease and diabetes. Other known names referring to such syndrome is syndrome X, insulin resistance syndrome, Reaven's syndrome. Several features of the syndromes include: fasting hyperglycemia, high blood pressure, central obesity (also known as visceral obesity), decreased High Density Lipoprotein (LDL), elevated triglycerides, elevated uric acid levels. Fasting hyperglycemia, listed above, includes diabetes mellitus type 2 or impaired fasting glucose and impaired glucose tolerance or insulin resistance. In addition to metabolic syndrome, the Notch decoy may have indications for pre-diabetic states.

Units, prefixes and symbols may be denoted in their SI accepted form. Unless otherwise indicated, nucleic acid sequences are written left to right in 5'to 3'orientation and amino acid sequences are written left to right in amino- to carboxy-terminal orientation. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The following abbreviations are used herein: ECD: extracellular domain; IC: intracellular domain; NECD/Fc: Notch-based fusion protein; N1: Notch1; N2: Notch2; N3: Notch3; N4: Notch4; Dll: Delta-like; DLL1: Delta-like 1; DLL4: Delta-like 4; JAG: JAGGED; JG: JAGGED; JAGGED-1: JAGGED 1; JG1: JAGGED 1; EC: endothelial cells; HUVEC: human umbilical vein endothelial cell; m.o.i.: multiplicity of infection; VEGF: vascular endothelial cell growth factor; VEGFR: vascular endothelial cell growth factor receptor; sp: signal peptide; PDGF: platelet derived growth factor; PDGFR: platelet derived growth factor receptor; P1GF: placental growth factor.

Embodiments of the Invention

This invention provides a fusion protein, the sequence of which, commencing at the N-terminus of the fusion protein, is identical to the sequence of amino acids in:
(a) an extracellular domain of a human Notch1 receptor protein, followed by
(b) an Fc portion of an antibody,
wherein the extracellular domain of the human Notch1 receptor protein
  (i) commences with the amino acid present at the N-terminus of EGF-like repeat 10 and
  (ii) extends to and includes the C-terminal amino acid of EGF-like repeat 18.

Also provided is a fusion protein, the sequence of which, commencing at the N-terminus of the fusion protein, is identical to the sequence of amino acids in:
(a) an extracellular domain of a human Notch1 receptor protein, followed by
(b) an Fc portion of an antibody,
wherein the extracellular domain of the human Notch1 receptor protein
  (i) commences with the amino acid present at the N-terminus of EGF-like repeat 10 and
  (ii) extends to and includes the C-terminal amino acid of EGF-like repeat 20.

Also provided is a fusion protein, the sequence of which, commencing at the N-terminus of the fusion protein, is identical to the sequence of amino acids in:
(a) an extracellular domain of a human Notch1 receptor protein, followed by
(b) a linker sequence, followed by
(c) an Fc portion of an antibody,
wherein the extracellular domain of the human Notch1 receptor protein
  (i) commences with the amino acid present at the N-terminus of EGF-like repeat 10 and
  (ii) extends to and includes the C-terminal amino acid of EGF-like repeat 18.

Also provided is a fusion protein, the sequence of which, commencing at the N-terminus of the fusion protein, is identical to the sequence of amino acids in:
(a) an extracellular domain of a human Notch1 receptor protein, followed by
(b) a linker sequence, followed by
(c) an Fc portion of an antibody,
wherein the extracellular domain of the human Notch1 receptor protein
  (i) commences with the amino acid present at the N-terminus of EGF-like repeat 10 and
  (ii) extends to and includes the C-terminal amino acid of EGF-like repeat 20.

Also provided is a fusion protein the sequence of which, commencing at the N-terminus of the fusion protein, is identical to the sequence of amino acids in:
(a) a signal peptide, followed by
(b) an extracellular domain of a human Notch1 receptor protein, followed by
(c) an Fc portion of an antibody,
wherein the extracellular domain of the human Notch1 receptor protein
  (i) commences with the amino acid present at the N-terminus of EGF-like repeat 10 and
  (ii) extends to and includes the C-terminal amino acid of EGF-like repeat 18.

Also provided is a fusion protein the sequence of which, commencing at the N-terminus of the fusion protein, is identical to the sequence of amino acids in:
(a) a signal peptide, followed by
(b) an extracellular domain of a human Notch1 receptor protein, followed by
(c) an Fc portion of an antibody,
wherein the extracellular domain of the human Notch1 receptor protein
  (i) commences with the amino acid present at the N-terminus of EGF-like repeat 10 and
  (ii) extends to and includes the C-terminal amino acid of EGF-like repeat 20.

In an embodiment of the fusion proteins of this invention, the signal peptide is the signal peptide of human Notch1 protein or the signal peptide of an IgG heavy chain.

In one embodiment of the fusion proteins of this invention, the Fc portion of the antibody is the Fc portion of a human antibody.

Also provided is a composition comprising any of the fusion proteins of this invention and a pharmaceutically acceptable carrier.

In one embodiment of the composition of this invention, the fusion protein is present in an amount effective to inhibit Jagged-Notch signaling.

In one embodiment of the composition of this invention, the fusion protein is present in an amount effective to inhibit Delta-like-Notch signaling.

Also provided is a method of treating a subject suffering from age-related macular degeneration (AMD) which comprises administering to the subject any of the compositions of the invention in an amount effective to treat the subject's AMD.

In one embodiment the AMD is wet AMD. In another embodiment the AMD is dry AMD.

Also provided is a method of treating a subject suffering from diabetic retinopathy which comprises administering to the subject any of the compositions of the invention in an amount effective to treat the subject's diabetic retinopathy.

In one embodiment of any of the methods of this invention, the method further comprises administering an inhibitor of Vascular Endothelial Growth Factor (VEGF). In one embodiment, the inhibitor of VEGF is an inhibitor of VEGF-A, PGIF, VEGF-B, VEGF-C, or VEGF-D.

In one embodiment of any of the methods of this invention, the method further comprises administering a VEGF receptor inhibitor. In one embodiment, the VEGF receptor inhibitor is a VEGFR-1 or a VEGFR-2 inhibitor.

Also provided is a method of treating a subject suffering from cancer which comprises administering to the subject any of the compositions of this invention in an amount effective to treat the subject's cancer. In one embodiment the cancer is pancreatic cancer. In another embodiment the cancer is breast cancer.

Also provided is a method of inhibiting angiogenesis or metastasis in a tumor in a subject, the method comprising administering to the subject any of the compositions of this invention in an amount effective to reduce angiogenesis or metastasis in the tumor.

Also provided is a method of inhibiting Jag1-specific Notch activation, the method comprising administering a composition of this invention comprising, the composition comprising a fusion protein of this invention wherein the extracellular domain of the human Notch1 receptor protein commences with the amino acid present at the N-terminus of EGF-like repeat 10 and extends to and includes the C-terminal amino acid of EGF-like repeat 20. In an embodiment the method does not inhibit Dll4-specific Notch activation. In an embodiment, the method inhibits angiogenic sprouting, cancer cell migration, and/or transendothelial migration of cancer cells across endothelial barriers.

Also provided is a method of inhibiting Jag1 and Dll4 Notch activation, the method comprising administering a composition of this invention comprising, the composition comprising a fusion protein of this invention wherein the extracellular domain of the human Notch1 receptor protein commences with the amino acid present at the N-terminus of EGF-like repeat 10 and extends to and includes the C-terminal amino acid of EGF-like repeat 18.

Each embodiment disclosed herein is contemplated as being applicable to each of the other disclosed embodiments. Thus, all combinations of the various elements described herein are within the scope of the invention.

EXAMPLES

Design of Notch1 Decoys

All decoys contain a designated number of EGF-like repeats from the extracellular domain of Notch1 fused at the C-terminus with human IgG1 Fc separated by a linker sequence. EGF-like repeats are designated in parentheses. Previous iterations of the decoys included Notch1 1-36, Notch1 1-13, and Notch1 10-24. Due to difficulty in producing relevant amounts of purified recombinant protein, inventors tested whether different variants of the decoys would be more easily secretable and examined ligand specificity with regards to inhibition of Notch activation. Using overlap extension PCR cloning, inventors were able to clone new variants including Notch1 10-22, Notch1 10-20, Notch1 10-18, and Notch1 10-16. See FIG. 3.

Notch1 Decoy Secretory Profile Shows Newer Decoys are Produced at Higher Levels than Previous Decoys.

Figure 4:
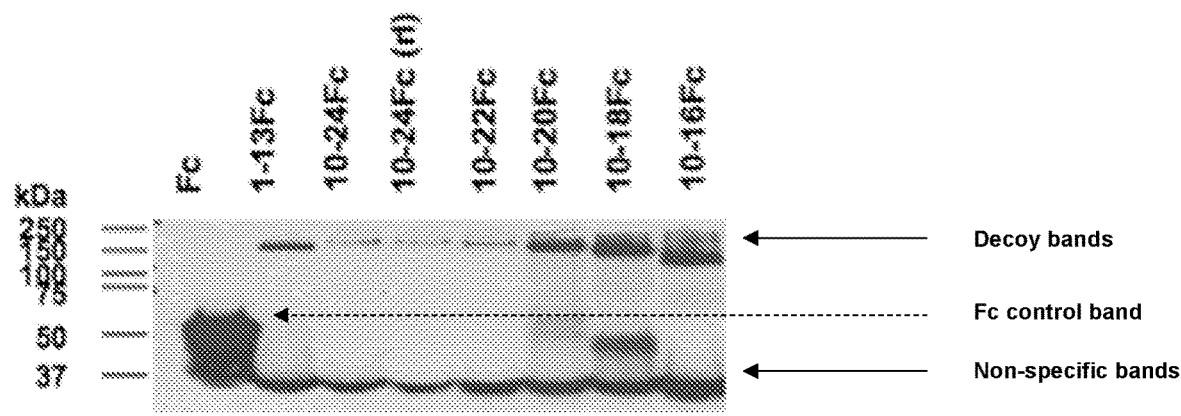
FIG. 4: Assay demonstrating that Notch1 10-20, 10-18, and 10-16 decoys are secreted at higher levels than Notch1 1-13 and 10-24 decoys.

Specific sequences coding for the cDNA of each decoy were cloned into a lentiviral expression construct, which was used to create chinese hamster ovary (CHO) cells stably expressing each decoy. CHO cells are the gold standard for recombinant biotherapeutic production. Conditioned media was collected from each CHO variant after 48 hours post-infection and equivalent volumes were evaluated by western blot analysis for visual, semi-quantitative determination of relative production. As expected, the Fc-only control is produced at the highest level. From our previous work, we observed that Notch1 1-13 is produced at higher amounts than Notch1 10-24. However, both are secreted at significantly lower amounts than Fc, and Notch1 10-24 is particularly difficult to produce. Notch1 10-24Fc(rl) represents a religated Notch1 10-24 as a control product of the cloning process. Notch1 10-22 appears to be secreted at a similar level as Notch1 10-24. However, Notch1 10-20 is secreted at even higher levels as Notch1 1-13 and Notch1 10-18 and Notch1 10-16 exhibit further enhanced secretion, providing three new potential decoys that are secreted at markedly higher levels than the previous decoys. See FIG. 4.

Ligand Specificity of Lentivirally-Expressed Notch1 Decoys.

Figure 5:
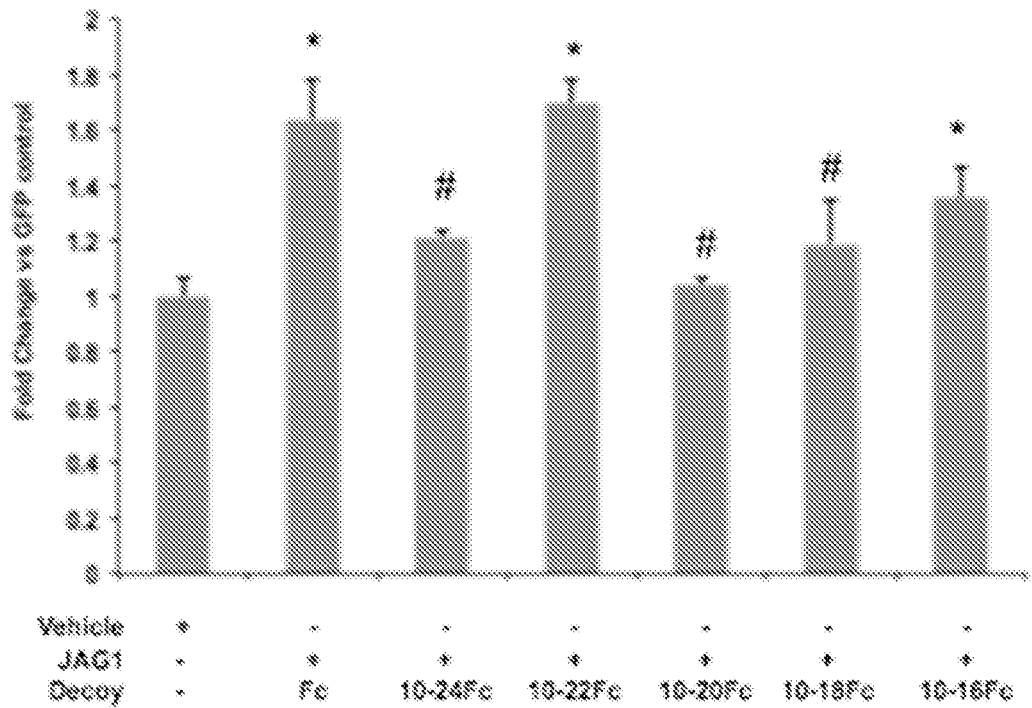
FIG. 5: Results of assay demonstrating that Notch1 10-20 decoy blocks Jag1-Notch and Notch1 10-18 decoy blocks both Jag1 and D114-Notch.
Figure 5:
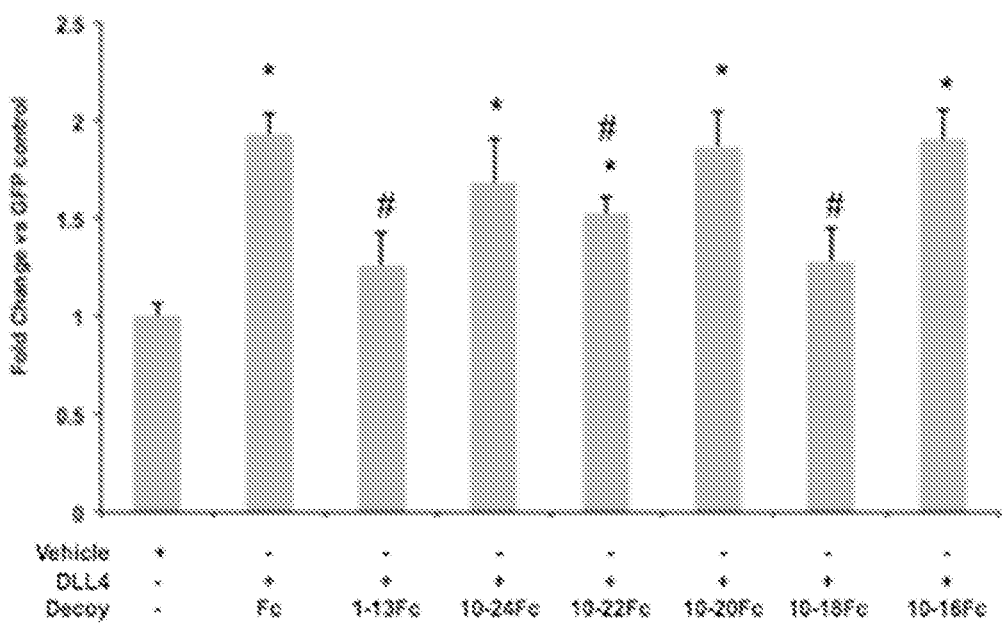

HeLa cells transfected with a Notch classical reporter construct to examine Notch activation were co-cultured with HeLa cells expressing a vehicle control (GFP-expressing construct), JAG1 overexpression construct, or a DLL4 overexpression construct. In addition, ligand-expressing HeLa cells were also infected to express Notch1 decoys or Fc control. As illustrated in FIG. 5, JAG1 and DLL4 both activate Notch. Notch1 10-24 and Notch1 1-13 inhibit JAG1 and DLL4-specific Notch activation, respectively, as previously observed. Notch1 10-22 does not inhibit JAG1-specific Notch activity, but does appear to reduce DLL4-specific Notch activity. Notch1 10-20 inhibits JAG1-specific Notch activity, but does not inhibit DLL4-specific Notch activity. Notch1 10-18 inhibits both JAG1 and DLL4-specific Notch activation, suggesting it may be a pan-Notch ligand inhibitor. Notch1 10-16 does not appear to inhibit either JAG1 or DLL4-specific Notch activation. These results show that of the newer decoys that are secreted at much higher levels than the previous decoys, Notch1 10-20 decoy retains Jagged specificity.

JAG1-Specific Notch1 10-20 Decoy is Produced and Secreted at Significantly Higher Levels and Maintains Structural Integrity After Purification.

Figure 6:
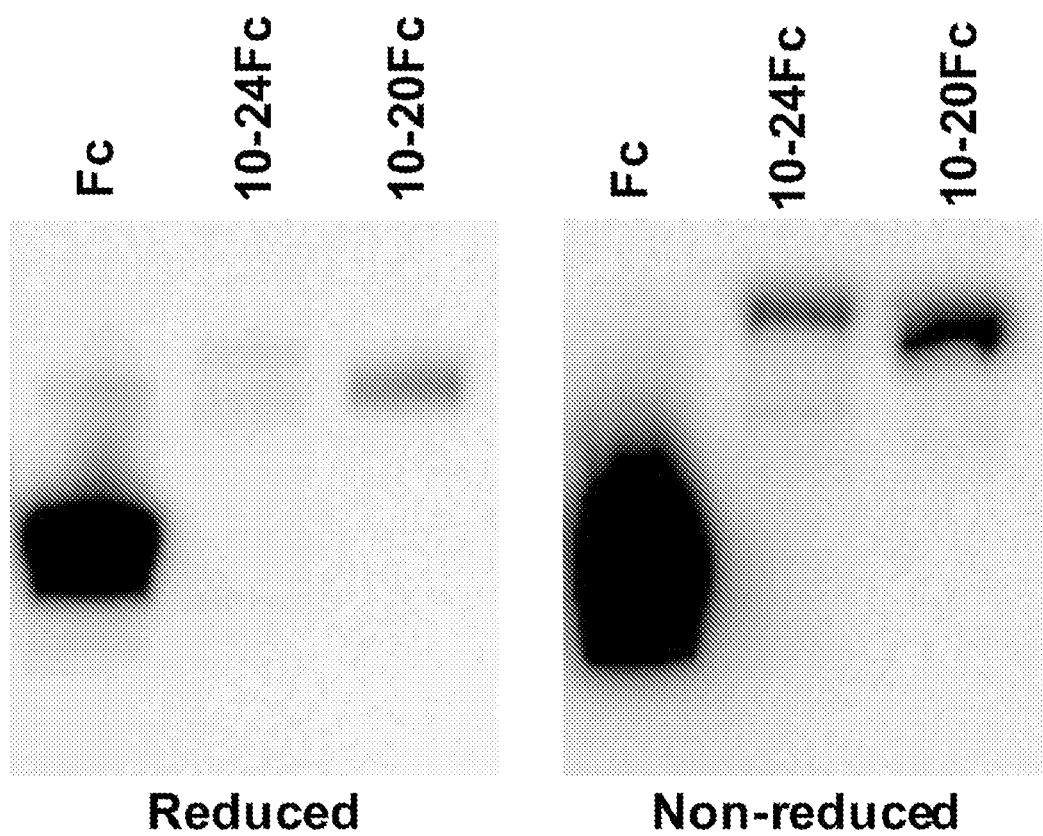
FIG. 6: Results of assay demonstrating that Notch1 10-20 decoy is secreted at higher levels than Notch1 10-24 decoy and maintains structural integrity after purification and storage.

Decoy-expressing suspension CHO cells were cultured in shaking flask bioreactors in animal-component free media and media were collected and protein produced was purified by affinity chromatography using protein A containing chromatography columns. After purification, protein was stored in phosphate buffered saline, frozen at −80 C, thawed and was analyzed by western blot analysis. Notch1 10-20 decoy is clearly produced at least two to three times more than Notch1 10-24 decoy without appreciable breakdown of the protein. Spectrophotometric analysis confirmed a 4-fold increase in production of Notch1 10-20 over Notch1 10-24, further confirming the potential of Notch1 10-20 as a Jag-specific decoy that can be produced at relevant levels and maintain structural integrity. See FIG. 6.

Purified Notch1 10-20 Decoy Inhibits Jag1-Specific Activation of Notch in a Jag1-Tethered Plate Assay.

Figure 7:
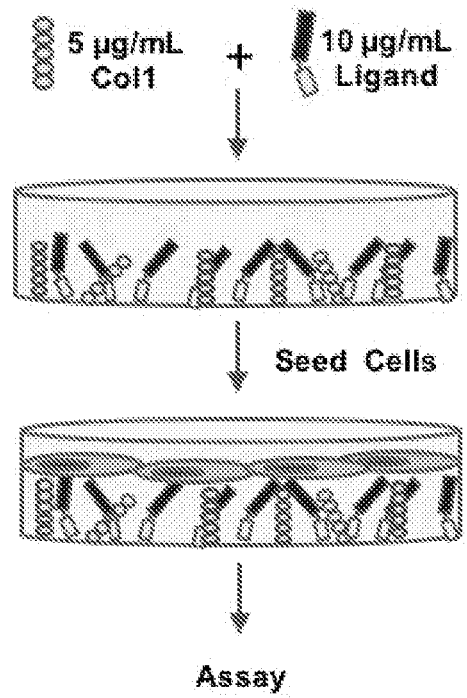
FIG. 7: Schematic depiction of assay and results of assay demonstrating that purified Notch1 10-20 decoy retains functional inhibition of Jag1-Notch activation.
Figure 7:
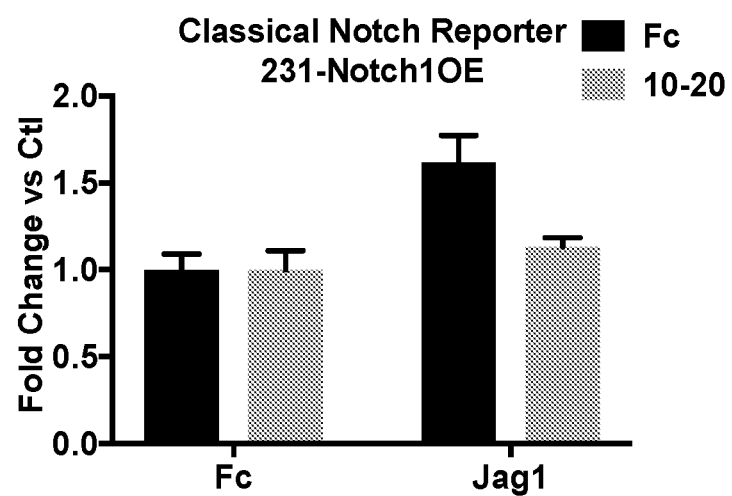

Jag1 protein adhered to cell culture plates along with fibronectin to promote cell attachment stimulated Notch activation of a classical Notch reporter in a dual luciferase reporter assay as measured after 24 hr of exposure of MDA-MB-231 triple negative breast cancer cells to Jag1. This Jag1-specific activation of Notch in the breast cancer cells was inhibited by 5 ug/mL of Notch1 10-20 purified decoy indicating that the purified decoy maintains inhibitory activity after purification and this can be easily evaluated in an in vitro test of activity using a tethered ligand approach. See FIG. 7.

Production/Secretion/Purification of New Decoys

Previously, Notch1 1-13, 1-24, and 10-24 decoys were difficult to produce and purify.

Cloning of novel decoys, Notch1 10-20 and 10-18 decoys has provided decoys that are much more highly produced/secreted and are able to be purified while retaining functional inhibition of ligand-specific Notch. Notch1 10-20 decoy inhibits Jag1-specific Notch activation and Notch1 10-18 inhibits both Dll4 and Jag1-specific Notch.

Functional Use of New Decoys

Notch1 1-13 decoy promotes angiogenic hypersprouting but leads to dysfunctional vasculature and reduced perfusion in tumors, while Notch1 1-24 and 10-24 decoys inhibit angiogenic sprouting and tumor perfusion.

The following sections of this example illustrate the anti-angiogenic activity and potential anti-metastatic activity of Notch1 10-20 decoy, initially performed by overexpressing decoy in endothelial or tumor cells.

The following data will be repeated with purified protein.

Lentivirally Expressed Notch1 10-20 Decoy Inhibits Angiogenesis More Robustly than Notch1 10-24 Decoy.

Figure 8:
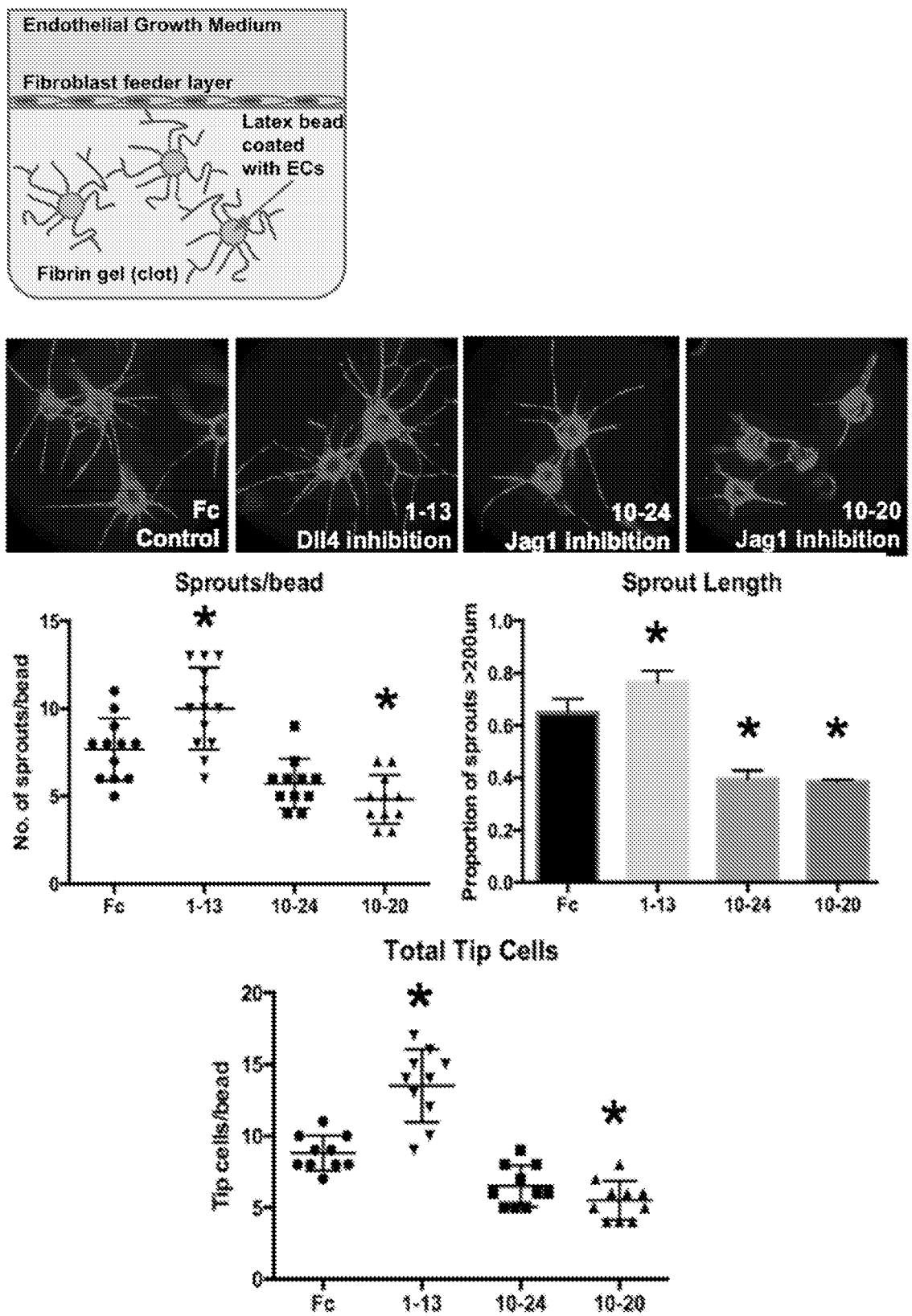
FIG. 8: Schematic depiction of assay and results of assay demonstrating that Notch1 10-20 decoy retains functional inhibition of sprouting angiogenesis similar to Notch1 10-24 Decoy.

As previously shown in PCT International Application Publication No. WO/2013/052607, Dll4-specific inhibition by Notch1 1-13 stimulates angiogenic hypersprouting in an in vitro fibrin bead angiogenesis assay, while inhibition of Jag1 by Notch1 10-24 leads to reduced sprouting angiogenesis. While Notch1 10-20 decoy is also Jag1 specific, it also inhibits angiogenesis, and in comparison to Notch1 10-24, Notch1 10-20 inhibited angiogenesis more robustly, most likely due to its greater secretion. See FIG. 8.

Notch1 Decoys Reduce Migration of Breast Cancer Cells in an Assay that Evaluates Metastatic Potential.

Figure 9:
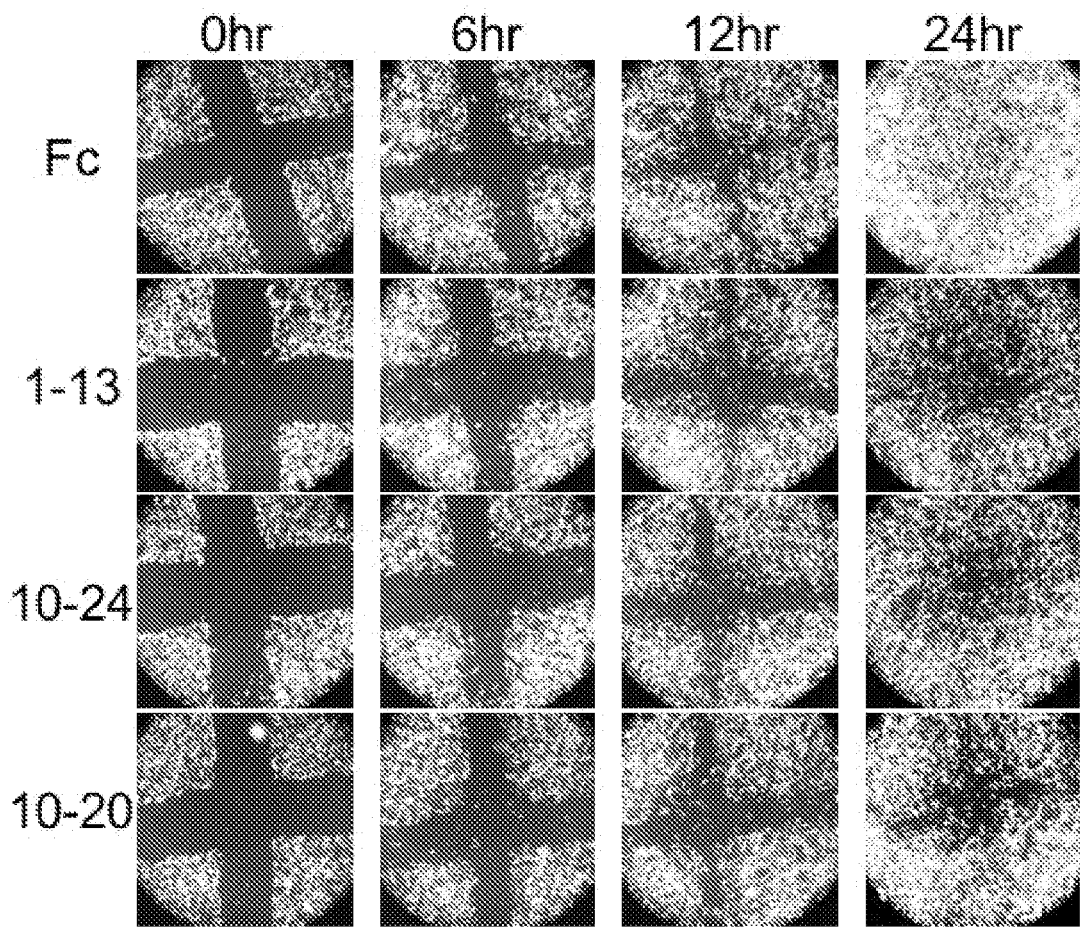
FIG. 9: Results of assay demonstrating that Notch1 1-13, 10-24, and 10-20 decoys inhibit migration of triple negative breast cancer cells.
Figure 9:
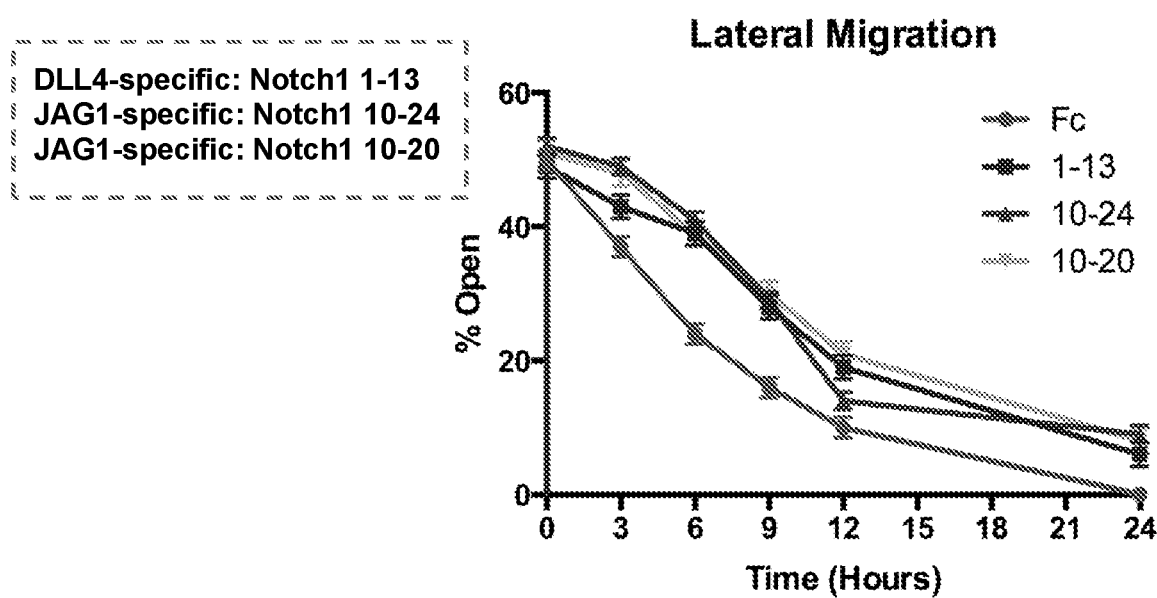

Notch inhibition by Notch1 1-13, Notch1 10-24, and Notch1 10-20 decoys delays lateral migration of MDA-MB-231 triple negative breast cancer cells in a wound closure assay. See FIG. 9.

Lentivirally Expressed Notch1 10-20 Decoy Inhibits Migration of Tumor Cells Across Endothelial Barriers Indicating its Potential as an Anti-Metastatic Jagged-Specific Notch Inhibitory Therapeutic.

Figure 10:
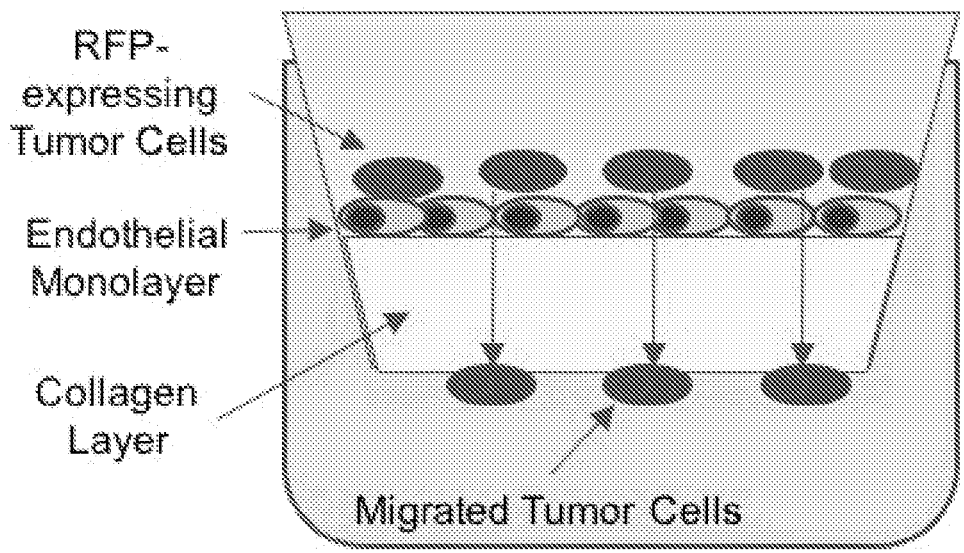
FIG. 10: Results of assay demonstrating that Notch1 10-20 decoy inhibits transendothelial migration of tumor cells across endothelial barriers.
Figure 10:
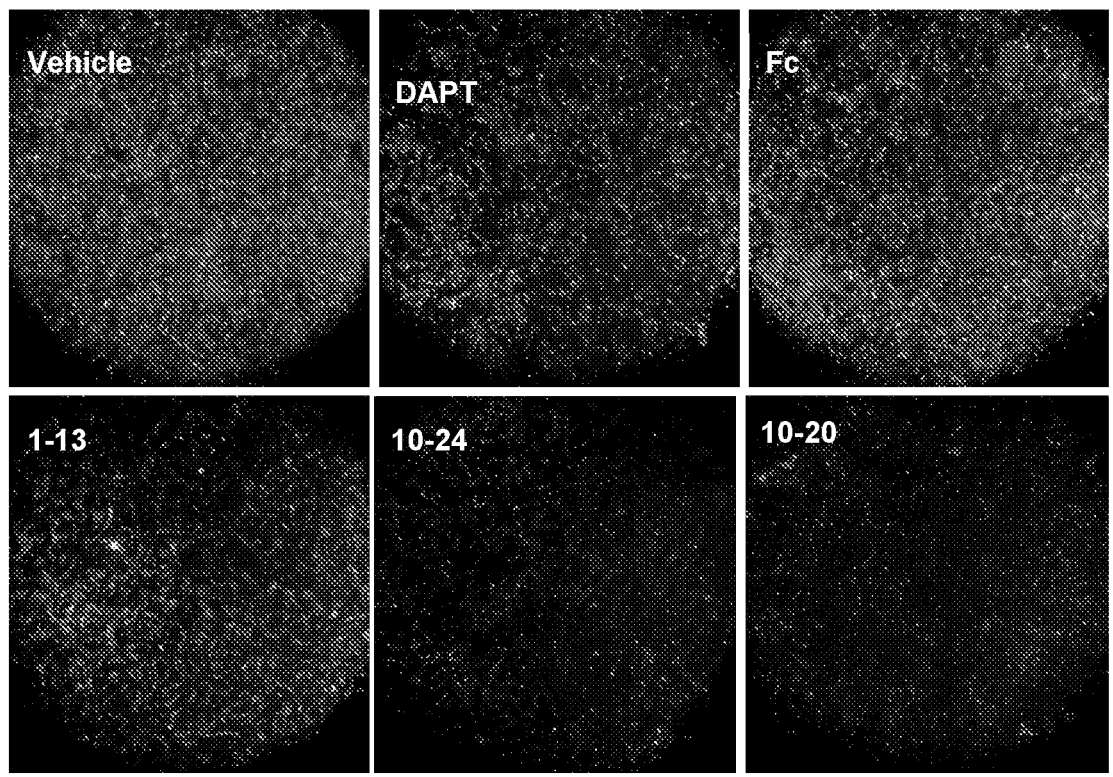

Non-specific Notch inhibition by the gamma secretase inhibitor DAPT and Dll4-specific inhibition by Notch1 1-13 decoy reduced transendothelial migration of MDA-MB-231 breast cancer cells across endothelial barriers, while Notch1 10-24 and Notch1 10-20 decoys robustly inhibited transendothelial migration. See FIG. 10.

Discussion

PCT International Application Publication No. WO/2013/052607, the contents of which are incorporated by reference, showed that Dll4-specific inhibition by Notch1 1-13 stimulates angiogenic hypersprouting in an in vitro fibrin bead angiogenesis assay, while inhibition of Jag1 by Notch1 10-24 leads to reduced sprouting angiogenesis. However, these previous decoys had the following limitations:
1. Decoys produced/secreted at low levels, suggesting manufacturing concerns for therapeutic production.
2. Due to difficulty in producing/secreting purified protein, functionality of purified decoys could not be thoroughly evaluated.

The objective of the new decoys was to achieve high production/secretion of decoys while maintaining ligand-specificity, and achieve functionality against angiogenesis, tumor growth, and other aspects of tumor progression such as metastasis.

What Inventors Have Achieved with New Decoys: Notch1 10-20 and Notch1 10-18 Decoys
1. Smaller decoys
2. Significantly greater production/secretion
3. Maintained ligand-specificity
4. Notch1 10-20 decoy is Jagged-specific, is produced/secreted at significantly higher levels than Notch1 10-24 decoy, inhibits in vitro angiogenic sprouting, inhibits cancer cell migration, and inhibits transendothelial migration of cancer cells across endothelial barriers.
5. Notch1 10-18 decoy appears to be a pan-ligand inhibitor. We must still evaluate its physiological function.

One major difference between the decoys of this invention and previous Notch inhibitors is that these decoys will specifically target Jagged-Notch or Dll-Notch signaling. Based on preliminary work targeting Jagged-Notch or Dll-Notch signaling, when used as therapeutics, these decoys will exhibit little to no toxic effects, which are seen with other Notch inhibitors.

A major improvement of the decoys of this invention is the fact that the general smaller size is designed to maximize potential to secrete and purify these decoys while still retaining the Notch ligand inhibitory properties. Thus they are a significant improvement on previously evaluated decoys, such as decoys comprising EGF-like repeats 10-24, 1-13 or 1-24.

What is claimed is:

1. A fusion protein, the sequence of which, commencing at the N-terminus of the fusion protein, is identical to the sequence of amino acids in:
   (a) an extracellular domain of a human Notch1 receptor protein, followed by
   (b) an Fc portion of an antibody,
   wherein the extracellular domain of the human Notch1 receptor protein
   (i) commences with the amino acid present at the N-terminus of EGF-like repeat 10 and
   (ii) extends to and includes the C-terminal amino acid of EGF-like repeat 18 as the C-terminal amino acid of the extracellular domain.

2. The fusion protein of claim 1, wherein the Fc portion of the antibody is the Fc portion of a human antibody.

3. A composition comprising the fusion protein of claim 1 and a pharmaceutically acceptable carrier.

4. The composition of claim 3, wherein the fusion protein is present in an amount effective to inhibit Jagged-Notch signaling.

5. The composition of claim 3, wherein the fusion protein is present in an amount effective to inhibit Delta-like-Notch signaling.

6. A method of treating a subject suffering from cancer which comprises administering to the subject the composition of claim 3 in an amount effective to treat the subject's cancer.

7. The method of claim 6, wherein the cancer is pancreatic cancer.

8. The method of claim 6, wherein the cancer is breast cancer.

9. A fusion protein, the sequence of which, commencing at the N-terminus of the fusion protein, is identical to the sequence of amino acids in:
   (a) an extracellular domain of a human Notch1 receptor protein, followed by
   (b) an Fc portion of an antibody,
   wherein the extracellular domain of the human Notch1 receptor protein
   (i) commences with the amino acid present at the N-terminus of EGF-like repeat 10 and
   (ii) extends to and includes the C-terminal amino acid of EGF-like repeat 20 as the C-terminal amino acid of the extracellular domain.

10. A fusion protein, the sequence of which, commencing at the N-terminus of the fusion protein, is identical to the sequence of amino acids in:
    (a) an extracellular domain of a human Notch1 receptor protein, followed by
    (b) a linker sequence, followed by
    (c) an Fc portion of an antibody,
    wherein the extracellular domain of the human Notch1 receptor protein
    (i) commences with the amino acid present at the N-terminus of EGF-like repeat 10 and
    (ii) extends to and includes the C-terminal amino acid of EGF-like repeat 18 as the C-terminal amino acid of the extracellular domain.

11. A fusion protein, the sequence of which, commencing at the N-terminus of the fusion protein, is identical to the sequence of amino acids in:
    (a) an extracellular domain of a human Notch1 receptor protein, followed by
    (b) a linker sequence, followed by
    (c) an Fc portion of an antibody,
    wherein the extracellular domain of the human Notch1 receptor protein
    (i) commences with the amino acid present at the N-terminus of EGF-like repeat 10 and
    (ii) extends to and includes the C-terminal amino acid of EGF-like repeat 20 as the C-terminal amino acid of the extracellular domain.

* * * * *

SEQUENCE LISTING

<160> NUMBER OF SEQ ID NOS: 3

<210> SEQ ID NO 1
<211> LENGTH: 2555
<212> TYPE: PRT

-continued

```
<213> ORGANISM: Homo sapiens

<400> SEQUENCE: 1

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400
```

-continued

Pro Ser Gly Tyr Thr Gly Pro Ala Cys Ser Gln Asp Val Asp Glu Cys
                    405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
            435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                    485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
            595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                    645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                    805                 810                 815

Cys Leu Leu Pro Tyr Thr Gly Ala Thr Cys Glu Val Val Leu Ala Pro

```
                   820                 825                 830
Cys Ala Pro Ser Pro Cys Arg Asn Gly Gly Glu Cys Arg Gln Ser Glu
            835                 840                 845

Asp Tyr Glu Ser Phe Ser Cys Val Cys Pro Thr Gly Trp Gln Gly Gln
850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
            885                 890                 895

Ala Gly Tyr Ser Gly Arg Asn Cys Glu Thr Asp Ile Asp Asp Cys Arg
                900                 905                 910

Pro Asn Pro Cys His Asn Gly Gly Ser Cys Thr Asp Gly Ile Asn Thr
            915                 920                 925

Ala Phe Cys Asp Cys Leu Pro Gly Phe Arg Gly Thr Phe Cys Glu Glu
            930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
            980                 985                 990

Phe Asn Gly Gly Thr Cys Val Asp Gly Ile Asn Ser Phe Thr Cys Leu
            995                1000                1005

Cys Pro Pro Gly Phe Thr Gly Ser Tyr Cys Gln His Asp Val Asn
       1010                1015                1020

Glu Cys Asp Ser Gln Pro Cys Leu His Gly Gly Thr Cys Gln Asp
       1025                1030                1035

Gly Cys Gly Ser Tyr Arg Cys Thr Cys Pro Gln Gly Tyr Thr Gly
       1040                1045                1050

Pro Asn Cys Gln Asn Leu Val His Trp Cys Asp Ser Ser Pro Cys
       1055                1060                1065

Lys Asn Gly Gly Lys Cys Trp Gln Thr His Thr Gln Tyr Arg Cys
       1070                1075                1080

Glu Cys Pro Ser Gly Trp Thr Gly Leu Tyr Cys Asp Val Pro Ser
       1085                1090                1095

Val Ser Cys Glu Val Ala Ala Gln Arg Gln Gly Val Asp Val Ala
       1100                1105                1110

Arg Leu Cys Gln His Gly Gly Leu Cys Val Asp Ala Gly Asn Thr
       1115                1120                1125

His His Cys Arg Cys Gln Ala Gly Tyr Thr Gly Ser Tyr Cys Glu
       1130                1135                1140

Asp Leu Val Asp Glu Cys Ser Pro Ser Pro Cys Gln Asn Gly Ala
       1145                1150                1155

Thr Cys Thr Asp Tyr Leu Gly Gly Tyr Ser Cys Lys Cys Val Ala
       1160                1165                1170

Gly Tyr His Gly Val Asn Cys Ser Glu Glu Ile Asp Glu Cys Leu
       1175                1180                1185

Ser His Pro Cys Gln Asn Gly Gly Thr Cys Leu Asp Leu Pro Asn
       1190                1195                1200

Thr Tyr Lys Cys Ser Cys Pro Arg Gly Thr Gln Gly Val His Cys
       1205                1210                1215

Glu Ile Asn Val Asp Asp Cys Asn Pro Pro Val Asp Pro Val Ser
       1220                1225                1230
```

```
Arg Ser Pro Lys Cys Phe Asn Asn Gly Thr Cys Val Asp Gln Val
    1235            1240                1245

Gly Gly Tyr Ser Cys Thr Cys Pro Pro Gly Phe Val Gly Glu Arg
    1250            1255                1260

Cys Glu Gly Asp Val Asn Glu Cys Leu Ser Asn Pro Cys Asp Ala
    1265            1270                1275

Arg Gly Thr Gln Asn Cys Val Gln Arg Val Asn Asp Phe His Cys
    1280            1285                1290

Glu Cys Arg Ala Gly His Thr Gly Arg Arg Cys Glu Ser Val Ile
    1295            1300                1305

Asn Gly Cys Lys Gly Lys Pro Cys Lys Asn Gly Gly Thr Cys Ala
    1310            1315                1320

Val Ala Ser Asn Thr Ala Arg Gly Phe Ile Cys Lys Cys Pro Ala
    1325            1330                1335

Gly Phe Glu Gly Ala Thr Cys Glu Asn Asp Ala Arg Thr Cys Gly
    1340            1345                1350

Ser Leu Arg Cys Leu Asn Gly Gly Thr Cys Ile Ser Gly Pro Arg
    1355            1360                1365

Ser Pro Thr Cys Leu Cys Leu Gly Pro Phe Thr Gly Pro Glu Cys
    1370            1375                1380

Gln Phe Pro Ala Ser Ser Pro Cys Leu Gly Gly Asn Pro Cys Tyr
    1385            1390                1395

Asn Gln Gly Thr Cys Glu Pro Thr Ser Glu Ser Pro Phe Tyr Arg
    1400            1405                1410

Cys Leu Cys Pro Ala Lys Phe Asn Gly Leu Leu Cys His Ile Leu
    1415            1420                1425

Asp Tyr Ser Phe Gly Gly Gly Ala Gly Arg Asp Ile Pro Pro Pro
    1430            1435                1440

Leu Ile Glu Glu Ala Cys Glu Leu Pro Glu Cys Gln Glu Asp Ala
    1445            1450                1455

Gly Asn Lys Val Cys Ser Leu Gln Cys Asn Asn His Ala Cys Gly
    1460            1465                1470

Trp Asp Gly Gly Asp Cys Ser Leu Asn Phe Asn Asp Pro Trp Lys
    1475            1480                1485

Asn Cys Thr Gln Ser Leu Gln Cys Trp Lys Tyr Phe Ser Asp Gly
    1490            1495                1500

His Cys Asp Ser Gln Cys Asn Ser Ala Gly Cys Leu Phe Asp Gly
    1505            1510                1515

Phe Asp Cys Gln Arg Ala Glu Gly Gln Cys Asn Pro Leu Tyr Asp
    1520            1525                1530

Gln Tyr Cys Lys Asp His Phe Ser Asp Gly His Cys Asp Gln Gly
    1535            1540                1545

Cys Asn Ser Ala Glu Cys Glu Trp Asp Gly Leu Asp Cys Ala Glu
    1550            1555                1560

His Val Pro Glu Arg Leu Ala Ala Gly Thr Leu Val Val Val Val
    1565            1570                1575

Leu Met Pro Pro Glu Gln Leu Arg Asn Ser Ser Phe His Phe Leu
    1580            1585                1590

Arg Glu Leu Ser Arg Val Leu His Thr Asn Val Val Phe Lys Arg
    1595            1600                1605

Asp Ala His Gly Gln Gln Met Ile Phe Pro Tyr Tyr Gly Arg Glu
    1610            1615                1620
```

-continued

Glu Glu Leu Arg Lys His Pro Ile Lys Arg Ala Ala Glu Gly Trp
1625                1630                1635

Ala Ala Pro Asp Ala Leu Leu Gly Gln Val Lys Ala Ser Leu Leu
1640                1645                1650

Pro Gly Gly Ser Glu Gly Gly Arg Arg Arg Glu Leu Asp Pro
1655                1660                1665

Met Asp Val Arg Gly Ser Ile Val Tyr Leu Glu Ile Asp Asn Arg
1670                1675                1680

Gln Cys Val Gln Ala Ser Ser Gln Cys Phe Gln Ser Ala Thr Asp
1685                1690                1695

Val Ala Ala Phe Leu Gly Ala Leu Ala Ser Leu Gly Ser Leu Asn
1700                1705                1710

Ile Pro Tyr Lys Ile Glu Ala Val Gln Ser Glu Thr Val Glu Pro
1715                1720                1725

Pro Pro Pro Ala Gln Leu His Phe Met Tyr Val Ala Ala Ala Ala
1730                1735                1740

Phe Val Leu Leu Phe Phe Val Gly Cys Gly Val Leu Leu Ser Arg
1745                1750                1755

Lys Arg Arg Arg Gln His Gly Gln Leu Trp Phe Pro Glu Gly Phe
1760                1765                1770

Lys Val Ser Glu Ala Ser Lys Lys Lys Arg Arg Glu Pro Leu Gly
1775                1780                1785

Glu Asp Ser Val Gly Leu Lys Pro Leu Lys Asn Ala Ser Asp Gly
1790                1795                1800

Ala Leu Met Asp Asp Asn Gln Asn Glu Trp Gly Asp Glu Asp Leu
1805                1810                1815

Glu Thr Lys Lys Phe Arg Phe Glu Glu Pro Val Val Leu Pro Asp
1820                1825                1830

Leu Asp Asp Gln Thr Asp His Arg Gln Trp Thr Gln Gln His Leu
1835                1840                1845

Asp Ala Ala Asp Leu Arg Met Ser Ala Met Ala Pro Thr Pro Pro
1850                1855                1860

Gln Gly Glu Val Asp Ala Asp Cys Met Asp Val Asn Val Arg Gly
1865                1870                1875

Pro Asp Gly Phe Thr Pro Leu Met Ile Ala Ser Cys Ser Gly Gly
1880                1885                1890

Gly Leu Glu Thr Gly Asn Ser Glu Glu Glu Glu Asp Ala Pro Ala
1895                1900                1905

Val Ile Ser Asp Phe Ile Tyr Gln Gly Ala Ser Leu His Asn Gln
1910                1915                1920

Thr Asp Arg Thr Gly Glu Thr Ala Leu His Leu Ala Ala Arg Tyr
1925                1930                1935

Ser Arg Ser Asp Ala Ala Lys Arg Leu Leu Glu Ala Ser Ala Asp
1940                1945                1950

Ala Asn Ile Gln Asp Asn Met Gly Arg Thr Pro Leu His Ala Ala
1955                1960                1965

Val Ser Ala Asp Ala Gln Gly Val Phe Gln Ile Leu Ile Arg Asn
1970                1975                1980

Arg Ala Thr Asp Leu Asp Ala Arg Met His Asp Gly Thr Thr Pro
1985                1990                1995

Leu Ile Leu Ala Ala Arg Leu Ala Val Glu Gly Met Leu Glu Asp
2000                2005                2010

Leu Ile Asn Ser His Ala Asp Val Asn Ala Val Asp Asp Leu Gly

```
            2015                2020                2025

Lys Ser Ala Leu His Trp Ala Ala Val Asn Asn Val Asp Ala
        2030            2035            2040

Ala Val Val Leu Leu Lys Asn Gly Ala Asn Lys Asp Met Gln Asn
    2045            2050            2055

Asn Arg Glu Glu Thr Pro Leu Phe Leu Ala Ala Arg Glu Gly Ser
    2060            2065            2070

Tyr Glu Thr Ala Lys Val Leu Leu Asp His Phe Ala Asn Arg Asp
    2075            2080            2085

Ile Thr Asp His Met Asp Arg Leu Pro Arg Asp Ile Ala Gln Glu
    2090            2095            2100

Arg Met His His Asp Ile Val Arg Leu Leu Asp Glu Tyr Asn Leu
    2105            2110            2115

Val Arg Ser Pro Gln Leu His Gly Ala Pro Leu Gly Gly Thr Pro
    2120            2125            2130

Thr Leu Ser Pro Pro Leu Cys Ser Pro Asn Gly Tyr Leu Gly Ser
    2135            2140            2145

Leu Lys Pro Gly Val Gln Gly Lys Lys Val Arg Lys Pro Ser Ser
    2150            2155            2160

Lys Gly Leu Ala Cys Gly Ser Lys Glu Ala Lys Asp Leu Lys Ala
    2165            2170            2175

Arg Arg Lys Lys Ser Gln Asp Gly Lys Gly Cys Leu Leu Asp Ser
    2180            2185            2190

Ser Gly Met Leu Ser Pro Val Asp Ser Leu Glu Ser Pro His Gly
    2195            2200            2205

Tyr Leu Ser Asp Val Ala Ser Pro Pro Leu Leu Pro Ser Pro Phe
    2210            2215            2220

Gln Gln Ser Pro Ser Val Pro Leu Asn His Leu Pro Gly Met Pro
    2225            2230            2235

Asp Thr His Leu Gly Ile Gly His Leu Asn Val Ala Ala Lys Pro
    2240            2245            2250

Glu Met Ala Ala Leu Gly Gly Gly Gly Arg Leu Ala Phe Glu Thr
    2255            2260            2265

Gly Pro Pro Arg Leu Ser His Leu Pro Val Ala Ser Gly Thr Ser
    2270            2275            2280

Thr Val Leu Gly Ser Ser Ser Gly Gly Ala Leu Asn Phe Thr Val
    2285            2290            2295

Gly Gly Ser Thr Ser Leu Asn Gly Gln Cys Glu Trp Leu Ser Arg
    2300            2305            2310

Leu Gln Ser Gly Met Val Pro Asn Gln Tyr Asn Pro Leu Arg Gly
    2315            2320            2325

Ser Val Ala Pro Gly Pro Leu Ser Thr Gln Ala Pro Ser Leu Gln
    2330            2335            2340

His Gly Met Val Gly Pro Leu His Ser Ser Leu Ala Ala Ser Ala
    2345            2350            2355

Leu Ser Gln Met Met Ser Tyr Gln Gly Leu Pro Ser Thr Arg Leu
    2360            2365            2370

Ala Thr Gln Pro His Leu Val Gln Thr Gln Val Gln Pro Gln
    2375            2380            2385

Asn Leu Gln Met Gln Gln Asn Leu Gln Pro Ala Asn Ile Gln
    2390            2395            2400

Gln Gln Gln Ser Leu Gln Pro Pro Pro Pro Pro Gln Pro His
    2405            2410            2415
```

```
Leu Gly Val Ser Ser Ala Ala Ser Gly His Leu Gly Arg Ser Phe
    2420            2425                2430

Leu Ser Gly Glu Pro Ser Gln Ala Asp Val Gln Pro Leu Gly Pro
    2435            2440                2445

Ser Ser Leu Ala Val His Thr Ile Leu Pro Gln Glu Ser Pro Ala
    2450            2455                2460

Leu Pro Thr Ser Leu Pro Ser Ser Leu Val Pro Pro Val Thr Ala
    2465            2470                2475

Ala Gln Phe Leu Thr Pro Pro Ser Gln His Ser Tyr Ser Ser Pro
    2480            2485                2490

Val Asp Asn Thr Pro Ser His Gln Leu Gln Val Pro Glu His Pro
    2495            2500                2505

Phe Leu Thr Pro Ser Pro Glu Ser Pro Asp Gln Trp Ser Ser Ser
    2510            2515                2520

Ser Pro His Ser Asn Val Ser Asp Trp Ser Glu Gly Val Ser Ser
    2525            2530                2535

Pro Pro Thr Ser Met Gln Ser Gln Ile Ala Arg Ile Pro Glu Ala
    2540            2545                2550

Phe Lys
    2555

<210> SEQ ID NO 2
<211> LENGTH: 2502
<212> TYPE: DNA
<213> ORGANISM: Artificial Sequence
<220> FEATURE:
<223> OTHER INFORMATION: Notch1 Decoy 10-24

<400> SEQUENCE: 2
atgccgccgc tcctggcgcc cctgctctgc ctggcgctgc tgcccgcgct cgccgcacga        60
ggcccgcgat gcatcagcaa cccctgtaac gagggctcca actgcgacac caaccctgtc      120
aatggcaagg ccatctgcac ctgcccctcg ggtacacgg gccggcctg cagccaggac        180 gtggatgagt gctcgctggg tgccaacccc tgcgagcatg cgggcaagtg catcaacacg      240
ctgggctcct tcgagtgcca gtgtctgcag ggctacacgg cccccgatg cgagatcgac       300 gtcaacgagt gcgtctcgaa cccgtgccag aacgacgcca cctgcctgga ccagattggg      360
gagttccagt gcatctgcat gccggctac gagggtgtgc actgcgaggt caacacagac       420
gagtgtgcca gcagcccctg cctgcacaat ggccgctgcc tggacaagat caatgagttc      480
cagtgcgagt gccccacggg cttcactggg catctgtgcc agtacgatgt ggacgagtgt      540
gccagcaccc cctgcaagaa tggtgccaag tgcctggacg acccaacac ttacacctgt       600 gtgtgcacgg aagggtacac ggggacgcac tgcgaggtgg acatcgatga gtgcgacccc      660 gaccctgcc actacggctc ctgcaaggac ggcgtcgcca ccttcacctg cctctgccgc       720
ccaggctaca cggccaccat ctgcgagacc aacatcaacg agtgctccag ccagccctgc      780
cgccacgggg gcacctgcca ggaccgcgac aacgcctacc tctgcttctg cctgaagggg      840
accacaggac ccaactgcga gatcaacctg gatgactgtg ccagcagccc ctgcgactcg      900
ggcacctgtc tggacaagat cgatggctac gagtgtgcct gtgagccggg ctacacaggg      960
agcatgtgta acatcaacat cgatgagtgt gcgggcaacc cctgccacaa cggggcacc      1020 tgcgaggacg gcatcaatgg cttcacctgc gctgccccg agggctacca cgacccacc      1080 tgcctgtctg aggtcaatga gtgcaacagc aaccctgcg tccacggggc ctgccggac       1140
```

| | | |
|---|---|---|
| agcctcaacg ggtacaagtg cgactgtgac cctgggtgga gtgggaccaa ctgtgacatc | 1200 |
| aacaacaatg agtgtgaatc caaccCttgt gtcaacggcg gcacctgcaa agacatgacc | 1260 |
| agtggctacg tgtgcacctg ccgggagggc ttcagcggtc ccaactgcca gaccaacatc | 1320 |
| aacgagtgtg cgtccaaccc atgtctgaac cagggcacgt gtattgacga cgttgccggg | 1380 |
| tacaagtgca actgcctgct gccctacaca ggtgccacgt gtgaggtggt gctggccccg | 1440 |
| tgtgccccca gccctgcag aaacggcggg gagtgcagg aatccgagga ctatgagagc | 1500 |
| ttctcctgtg tctgccccac gggctggcaa gggcagacct gtgaggtcga catcaacgag | 1560 |
| tgcgttctga cccgtgccg gcacggcgca tcctgccaga cacccacgg cggctaccgc | 1620 |
| tgccactgcc aggccggcta cagtgggcgc aactgcgaga ccgacatcga cgactgccgg | 1680 |
| cccaacccgt gtcacaacgg gggctcctgc acagacggca tcaacacggc cttctgcgac | 1740 |
| tgcctgcccg gcttccgggg cactttctgt gaggaggaca tcaacgagga tctgggcccg | 1800 |
| ggcgagccca atcttgtga caaaactcac acatgcccac cgtgcccagc acctgaactc | 1860 |
| ctggggggac cgtcagtctt cctcttcccc ccaaaaccca aggacaccct catgatctcc | 1920 |
| cggacccctg aggtcacatg cgtggtggtg gacgtgagcc acgaagaccc tgaggtcaag | 1980 |
| ttcaactggt acgtggacgg cgtggaggtg cataatgcca agacaaagcc gcggaggag | 2040 |
| cagtacaaca gcacgtaccg tgtggtcagc gtcctcaccg tcctgcacca ggactggctg | 2100 |
| aatggcaagg agtacaagtg caaggtctcc aacaaagccc tcccagcccc catcgagaaa | 2160 |
| accatctcca agccaaagg cagccccga gaaccacagg tgtacaccct gcccccatcc | 2220 |
| cgggaggaga tgaccaagaa ccaggtcagc ctgacctgcc tggtcaaagg cttctatccc | 2280 |
| agcgacatcg ccgtggagtg ggagagcaat gggcagccgg agaacaacta caagaccacg | 2340 |
| cctcccgtgc tggactccga cggctccttc ttcctctaca gcaagctcac cgtggacaag | 2400 |
| agcaggtggc agcaggggaa cgtcttctca tgctccgtga tgcatgaggc tctgcacaac | 2460 |
| cactacacgc agaagagcct ctccctgtct ccgggtaaat ga | 2502 |

<210> SEQ ID NO 3
<211> LENGTH: 833
<212> TYPE: PRT
<213> ORGANISM: Artificial Sequence
<220> FEATURE:
<223> OTHER INFORMATION: Notch1 Decoy 10-24

<400> SEQUENCE: 3

```
Met Pro Pro Leu Leu Ala Pro Leu Leu Cys Leu Ala Leu Leu Pro Ala
1               5                   10                  15

Leu Ala Ala Arg Gly Pro Arg Cys Ile Ser Asn Pro Cys Asn Glu Gly
            20                  25                  30

Ser Asn Cys Asp Thr Asn Pro Val Asn Gly Lys Ala Ile Cys Thr Cys
        35                  40                  45

Pro Ser Gly Tyr Thr Gly Pro Ala Cys Ser Gln Asp Val Asp Glu Cys
    50                  55                  60

Ser Leu Gly Ala Asn Pro Cys Glu His Ala Gly Lys Cys Ile Asn Thr
65                  70                  75                  80

Leu Gly Ser Phe Glu Cys Gln Cys Leu Gln Gly Tyr Thr Gly Pro Arg
                85                  90                  95

Cys Glu Ile Asp Val Asn Glu Cys Val Ser Asn Pro Cys Gln Asn Asp
            100                 105                 110

Ala Thr Cys Leu Asp Gln Ile Gly Glu Phe Gln Cys Ile Cys Met Pro
        115                 120                 125
```

```
Gly Tyr Glu Gly Val His Cys Glu Val Asn Thr Asp Glu Cys Ala Ser
            130                 135                 140
Ser Pro Cys Leu His Asn Gly Arg Cys Leu Asp Lys Ile Asn Glu Phe
145                 150                 155                 160
Gln Cys Glu Cys Pro Thr Gly Phe Thr Gly His Leu Cys Gln Tyr Asp
                165                 170                 175
Val Asp Glu Cys Ala Ser Thr Pro Cys Lys Asn Gly Ala Lys Cys Leu
            180                 185                 190
Asp Gly Pro Asn Thr Tyr Thr Cys Val Cys Thr Glu Gly Tyr Thr Gly
            195                 200                 205
Thr His Cys Glu Val Asp Ile Asp Glu Cys Asp Pro Asp Pro Cys His
        210                 215                 220
Tyr Gly Ser Cys Lys Asp Gly Val Ala Thr Phe Thr Cys Leu Cys Arg
225                 230                 235                 240
Pro Gly Tyr Thr Gly His His Cys Glu Thr Asn Ile Asn Glu Cys Ser
                245                 250                 255
Ser Gln Pro Cys Arg His Gly Gly Thr Cys Gln Asp Arg Asp Asn Ala
            260                 265                 270
Tyr Leu Cys Phe Cys Leu Lys Gly Thr Thr Gly Pro Asn Cys Glu Ile
        275                 280                 285
Asn Leu Asp Asp Cys Ala Ser Ser Pro Cys Asp Ser Gly Thr Cys Leu
        290                 295                 300
Asp Lys Ile Asp Gly Tyr Glu Cys Ala Cys Glu Pro Gly Tyr Thr Gly
305                 310                 315                 320
Ser Met Cys Asn Ile Asn Ile Asp Glu Cys Ala Gly Asn Pro Cys His
                325                 330                 335
Asn Gly Gly Thr Cys Glu Asp Gly Ile Asn Gly Phe Thr Cys Arg Cys
            340                 345                 350
Pro Glu Gly Tyr His Asp Pro Thr Cys Leu Ser Glu Val Asn Glu Cys
            355                 360                 365
Asn Ser Asn Pro Cys Val His Gly Ala Cys Arg Asp Ser Leu Asn Gly
        370                 375                 380
Tyr Lys Cys Asp Cys Asp Pro Gly Trp Ser Gly Thr Asn Cys Asp Ile
385                 390                 395                 400
Asn Asn Asn Glu Cys Glu Ser Asn Pro Cys Val Asn Gly Gly Thr Cys
                405                 410                 415
Lys Asp Met Thr Ser Gly Tyr Val Cys Thr Cys Arg Glu Gly Phe Ser
            420                 425                 430
Gly Pro Asn Cys Gln Thr Asn Ile Asn Glu Cys Ala Ser Asn Pro Cys
            435                 440                 445
Leu Asn Gln Gly Thr Cys Ile Asp Asp Val Ala Gly Tyr Lys Cys Asn
        450                 455                 460
Cys Leu Leu Pro Tyr Thr Gly Ala Thr Cys Glu Val Val Leu Ala Pro
465                 470                 475                 480
Cys Ala Pro Ser Pro Cys Arg Asn Gly Gly Glu Cys Arg Gln Ser Glu
                485                 490                 495
Asp Tyr Glu Ser Phe Ser Cys Val Cys Pro Thr Gly Trp Gln Gly Gln
            500                 505                 510
Thr Cys Glu Val Asp Ile Asn Glu Cys Val Leu Ser Pro Cys Arg His
        515                 520                 525
Gly Ala Ser Cys Gln Asn Thr His Gly Gly Tyr Arg Cys His Cys Gln
        530                 535                 540
```

-continued

```
Ala Gly Tyr Ser Gly Arg Asn Cys Glu Thr Asp Ile Asp Asp Cys Arg
545                 550                 555                 560

Pro Asn Pro Cys His Asn Gly Gly Ser Cys Thr Asp Gly Ile Asn Thr
            565                 570                 575

Ala Phe Cys Asp Cys Leu Pro Gly Phe Arg Gly Thr Phe Cys Glu Glu
            580                 585                 590

Asp Ile Asn Glu Asp Leu Gly Pro Gly Pro Lys Ser Cys Asp Lys
        595                 600                 605

Thr His Thr Cys Pro Pro Cys Pro Ala Pro Glu Leu Leu Gly Gly Pro
        610                 615                 620

Ser Val Phe Leu Phe Pro Pro Lys Pro Lys Asp Thr Leu Met Ile Ser
625                 630                 635                 640

Arg Thr Pro Glu Val Thr Cys Val Val Val Asp Val Ser His Glu Asp
                645                 650                 655

Pro Glu Val Lys Phe Asn Trp Tyr Val Asp Gly Val Glu Val His Asn
                660                 665                 670

Ala Lys Thr Lys Pro Arg Glu Glu Gln Tyr Asn Ser Thr Tyr Arg Val
            675                 680                 685

Val Ser Val Leu Thr Val Leu His Gln Asp Trp Leu Asn Gly Lys Glu
        690                 695                 700

Tyr Lys Cys Lys Val Ser Asn Lys Ala Leu Pro Ala Pro Ile Glu Lys
705                 710                 715                 720

Thr Ile Ser Lys Ala Lys Gly Gln Pro Arg Glu Pro Gln Val Tyr Thr
                725                 730                 735

Leu Pro Pro Ser Arg Glu Glu Met Thr Lys Asn Gln Val Ser Leu Thr
            740                 745                 750

Cys Leu Val Lys Gly Phe Tyr Pro Ser Asp Ile Ala Val Glu Trp Glu
        755                 760                 765

Ser Asn Gly Gln Pro Glu Asn Asn Tyr Lys Thr Thr Pro Pro Val Leu
770                 775                 780

Asp Ser Asp Gly Ser Phe Phe Leu Tyr Ser Lys Leu Thr Val Asp Lys
785                 790                 795                 800

Ser Arg Trp Gln Gln Gly Asn Val Phe Ser Cys Ser Val Met His Glu
                805                 810                 815

Ala Leu His Asn His Tyr Thr Gln Lys Ser Leu Ser Leu Ser Pro Gly
            820                 825                 830

Lys
```